(12) United States Patent
Cipolletti et al.

(10) Patent No.: US 10,308,675 B2
(45) Date of Patent: Jun. 4, 2019

(54) HYDRATED AND ANHYDROUS POLYMORPHS OF 2'-O-FUCOSYLLACTOSE AND THEIR PRODUCTION METHODS

(71) Applicant: INALCO S.A.S. DI GIOVANNI CIPOLLETTI & C., Milan (IT)

(72) Inventors: Giovanni Cipolletti, Milan (IT); Gessica Laudati, Scandicci (IT); Liana Salsini, Seravezza (IT)

(73) Assignee: Inalco S.A.S. Di Giovanni Cipolletti & C., Milan (IT)

( * ) Notice: Subject to any disclaimer, the term of this patent is extended or adjusted under 35 U.S.C. 154(b) by 369 days.

(21) Appl. No.: 14/655,470

(22) PCT Filed: Jul. 12, 2013

(86) PCT No.: PCT/IB2013/055744
§ 371 (c)(1),
(2) Date: Jun. 25, 2015

(87) PCT Pub. No.: WO2014/009921
PCT Pub. Date: Jan. 16, 2014

(65) Prior Publication Data
US 2016/0060283 A1    Mar. 3, 2016

(30) Foreign Application Priority Data

Jul. 12, 2012 (IT) .................. FI2012A0143

(51) Int. Cl.
*C07H 3/06* (2006.01)
(52) U.S. Cl.
CPC ..................... *C07H 3/06* (2013.01)
(58) Field of Classification Search
None
See application file for complete search history.

(56) References Cited

FOREIGN PATENT DOCUMENTS

| WO | 2010115934 A1 | 10/2010 |
|---|---|---|
| WO | 2011150939 A1 | 12/2011 |

OTHER PUBLICATIONS

Morissette, S. et al., Advanced Drug Delivery Reviews, "High-throughput crystallization: polymorphs, salts, co-crystals and solvates of pharmaceutical solids", 2004, vol. 56, pp. 275-300 (Year: 2004).*
Vippagunta, S. et al., Advanced Drug Delivery Reviews, "Crystalline solids", 2001, vol. 48, pp. 3-26 (Year: 2001).*
Caira M.R.; "Crystalline Polymorphism of Organic Compounds", Topics in Current Chemistry, Springer, Berlin, DE, Jan. 1, 1998.
Notification of Transmittal of the International Search Report and the Written Opinion of the International Searching Authority, or the Declaration for International Application No. PCT/IB2013/055744 dated Jan. 28, 2014.

* cited by examiner

*Primary Examiner* — Shaojia A Jiang
*Assistant Examiner* — Bahar Craigo
(74) *Attorney, Agent, or Firm* — Abelman, Frayne & Schwab

(57) ABSTRACT

This invention describes new hydrated and anhydrous polymorphs of 2'-0-fucosyllactose (2'FL): Polymorph A 2'FL-3/2H$_2$O, Polymorph B 2TL-5/2 H$_2$O and anhydrous Polymorph C. There is also a description of the methods for obtaining them, and of a new method for preparing Polymorph I already known in the literature.

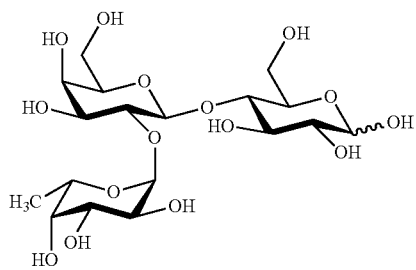

Diagram 1

15 Claims, 33 Drawing Sheets

XRPD Polymorph A (Example 1)

IR spectrum Polymorph A (Example 2)

DSC Polymorph A (Example 2)

XRPD Polymorph A (Example 2)

ORTEP diagram of the structure from XRPD single crystal Polymorph A (Example 2)

TGA and DTA Polymorph A (Example 2)

XRPD Polymorph A (Example 4)

XRPD Polymorph A (Example 6)

IR spectrum Polymorph A (Example 6)

XRPD Polymorph A (Example 7)

IR spectrum Polymorph A (Example 7)

IR spectrum Polymorph A (Example 8)

XRPD Polymorph A (Example 8)

XRPD Polymorph A (Example 9)

XRPD Polymorph A (Example 10)

¹HNMR Polymorph A (Example 11)

XRPD Polymorph A (Example 13)

Thermodiffractometry (Example 14)

IR spectrum Polymorph B (Example 15)

XRPD Polymorph B (Example 15)

IR spectrum Polymorph B (Example 17)

DSC Polymorph B (Example 17)

TGA and DTA Polymorph B (Example 17)

XRPD Polymorph B (Example 17)

¹HNMR Polymorph B (Example 18)

¹NMR Polymorph C (Example 19)

IR Polymorph C (Example 19)

DSC Polymorph C (Example 19)

XRPD Polymorph C (Example 19)

IR spectrum Polymorph C (Example 20)

XRPD Polymorph C (Example 20)

¹HNMR Polymorph I (Example 21)

XRPD Polymorph I (Example 21)

HYDRATED AND ANHYDROUS POLYMORPHS OF 2'-O-FUCOSYLLACTOSE AND THEIR PRODUCTION METHODS

CROSS-REFERENCE TO RELATED APPLICATIONS

This application is a National Phase of PCT/IB2013/055744, filed 12 Jul. 2013, which claims priority from Italian Application No. FI-2012-A000143 filed 12 Jul. 2012, the disclosures of which are all incorporated herein by reference.

FIELD OF THE INVENTION

This invention relates to the field of new hydrate compounds and one anhydrous polymorph of 2'-O-fucosyllactose (2'FL) and their methods of preparation, and in particular refers to two new hydrate and anhydrous polymorphs.

STATE OF THE ART

In recent years, many efforts have been made to synthesise oligosaccharides, given their involvement in numerous biological processes. Much importance, from a commercial point of view, has been given to oligosaccharides secreted in human milk, both for their food value and for their therapeutic role. One of the main ones, present in the highest concentrations, is 2'FL (Diagram 1 shows the structural formula) not only important from a nutritional and probiotic point of view, but also due to its anti-adhesiveness, immunostimulation, neuronal development etc. . . .

Diagram 1

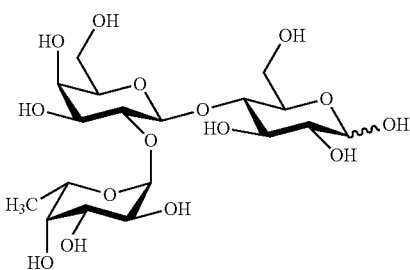

An interesting commercial objective is to use this oligosaccharide in baby foods such as infant formula, nutritional supplements, or cosmetic and pharmaceutical formulations. To do this one would need to have a simple and cheap method of isolation and purification, such as crystallisation.

The first samples of oligosaccharides secreted in human milk, were obtained by chromatography of the milk itself, with purities that were not very high, given the large number of structural isomers present. In the specific case of 2'-O-Fucosyllactose, the presence of the structural isomer 3-O-Fucosyllactose made its isolation difficult for a long time.

Note that the various crystalline or amorphous phases of an active molecule (such as 2'FL), may possess chemical, physical, and mechanical properties that may be quite different from one another (e.g. solubility and bioavailability, hygroscopicity, thermal and electrical conductivity, chemical stability, hardness, etc.), with considerable consequences on their use, handling, and purification. Furthermore, the possibility of interconversion between the various forms can have very serious consequences on the life of a product and on the maintenance of the desired properties (therapeutic efficacy in the case of a drug, chromatic properties in the case of a pigment, etc.). More specifically, it should be considered that, depending on variables such as temperature, pressure, and relative humidity, a metastable form can be transformed into a thermodynamically more stable form, or else an anhydrous crystalline form can be transformed into a hydrate crystalline form by the absorption of water vapour from the environment, and a solvate crystalline form can, in turn, be transformed into an anhydrous crystalline form or one with a different degree of solvation due to solvent loss.

Regarding 2'FL the first crystalline form is given in the literature by Kuhn et al. (Chem. Ber. 1955, 88, 1135; ibid., 1956, 89, 2513), which describe the crystallisation of the oligosaccharide isolated from human milk. They obtain a crystal that has no hydration water, which they believe to be in a anomeric form and which has a melting point (with decomposition) of 230-231° C. As described by Kuhn this crystalline form can be obtained from the 2'FL isolated from human milk (as syrup or amorphous) dissolving it in 75% hot methanol to which, in the presence of seed crystals, absolute ethanol is gradually added. The seed crystals were obtained because, after prolonged storage, they were found to be precipitated on the walls of the flasks containing the 2'FL syrup or else precipitated from a solution of aqueous methanol, n-butanol, and n-hexanol at 4° C. for several weeks.

After Kuhn, crystalline forms are disclosed in patent application WO/2011 150939 where there are reported two polymorphs of 2'-O-Fucosyllactose therein named Polymorph I and Polymorph II.

Polymorph I has an X-ray powder diffraction with characteristic peaks at angles $2\theta 21.34°$, $20.92°$, $18.37°$, $16.70°$, $9.91°$, $13.13°$, $7.87°$ and $8.90°$. Polymorph I is described as being predominantly in a anomeric form, free of crystallisation water or solvent and with an endothermic DSC curve whose maximum peak is at $260\pm1°$ C. or $246\pm1°$ C. as the $\beta$ anomer percentage decreases (from $20\pm3\%$ to $12\pm3\%$). This Polymorph I is described as being obtainable by crystallisation, in the absence of seed crystals, from an aqueous mixture of methanol or ethanol. Polymorph II has an X-ray powder diffraction with characteristic peaks at angles $2\theta$ $16.98°$, $13.65°$, $18.32°$, $21.70°$, $15.22°$, $20.63°$ and $11.94°$. Polymorph II is described as anhydrous and non-solvate. It can be a mixture of the two anomers or else just one of the two. This, in DSC, presents an endothermic curve which has a maximum peak at $259.5\pm2°$ C. This Polymorph II is described as being obtainable by crystallisation, in the presence of seed crystals, from an aqueous mixture of methanol, or alternatively can be obtained by crystallisation, without seed, from Polymorph I from ethyl acetate.

For the production of 2FL the need is still felt to gain more knowledge relating to its possible crystalline forms so as to improve the characteristics of the product and improve long-term possibilities for production, purification, and shelf-life.

The purpose of this invention is to provide further polymorphs of 2'FL and their preparation methods, which would preferably be industrially exploitable.

Definitions and Abbreviations

XRPD: X-ray powder diffraction
IR: infrared
DSC: differential scanning calorimetry
NMR: nuclear magnetic resonance
TGA: thermogravimetric analysis DTA: differential thermal analysis
LOD=loss on drying
KF: Karl Fischer

SUMMARY OF THE INVENTION

This invention solves the above problems through the isolation and identification of new hydrate compounds and a new anhydrous polymorph of 2'FL:
Hydrate compounds with general formula 2'FL.nH$_2$O where n is a number between 1 and 3.
Anhydrous 2'FL in the form of Polymorph C with characteristic XRPD peaks at 17.58±0.20, 17.44±0.20, 10.63±0.20 2θ,
In particular the following two new hydrate compounds have been identified:
2'FL.3/2 H$_2$O, preferably in the crystalline form of Polymorph A with characteristic XRPD peaks at 18.86±0.20, 9.89±0.20, 17.05±0.20 2θ,
2'FL.5/2 H$_2$O, preferably in the crystalline form of Polymorph B with characteristic XRPD peaks at 9.96±0.20, 18.56±0.20, 20.48±0.20 2θ, This invention also relates to methods of preparing these polymorphs and also provides, by crystallisation from glacial acetic acid, a new alternative method for preparing Polymorph I previously described in WO2011/150939.

Surprisingly the isolation of the polymorphs of 2'-O-Fucosyllactose according to the invention is easily feasible with excellent yields on an industrial scale. In particular, in fact, Polymorphs A and B are isolated, at the end of the 2'FL synthesis process, with high purity, and can therefore be used as ingredients in various types of pharmaceutical or food formulations.

DETAILED DESCRIPTION OF THE INVENTION

For the purposes of this invention X-ray powder diffractometry refers to measurements made using Cu-Kα radiation.

To obtain the new hydrate compounds and the new anhydrous polymorph of this invention, the 2'FL could have been obtained by way of extraction, enzymatically, chemically (for example see synthesis procedures described in WO 2010/070616, WO 2010/115934, WO 2010/115935), or by a combination of these ways.

This invention also relates to a method for obtaining Polymorph A which is obtained by crystallisation from a mixture comprising water and at least one other solvent. Said solvent may be selected from alcohols, ketones (e.g. acetone), nitriles (e.g. acetonitrile), organic acids (for example glacial acetic acid), or esters (e.g. ethyl acetate). The preferred solvents are C1-C3 alcohol and in particular C2 alcohol and crystallisation can be conducted either with or without seeding.

The water to solvent ratio can vary between 40 and 10% (v/v), and the preferred amount is between 25 and 15% (v/v).

Polymorph A is 3/2 hydrate, and with a solvent content of less than 1100 ppm, preferably less than 550 ppm, still more preferably less than 200 ppm and in particular less than 100 ppm.

Figure 5:
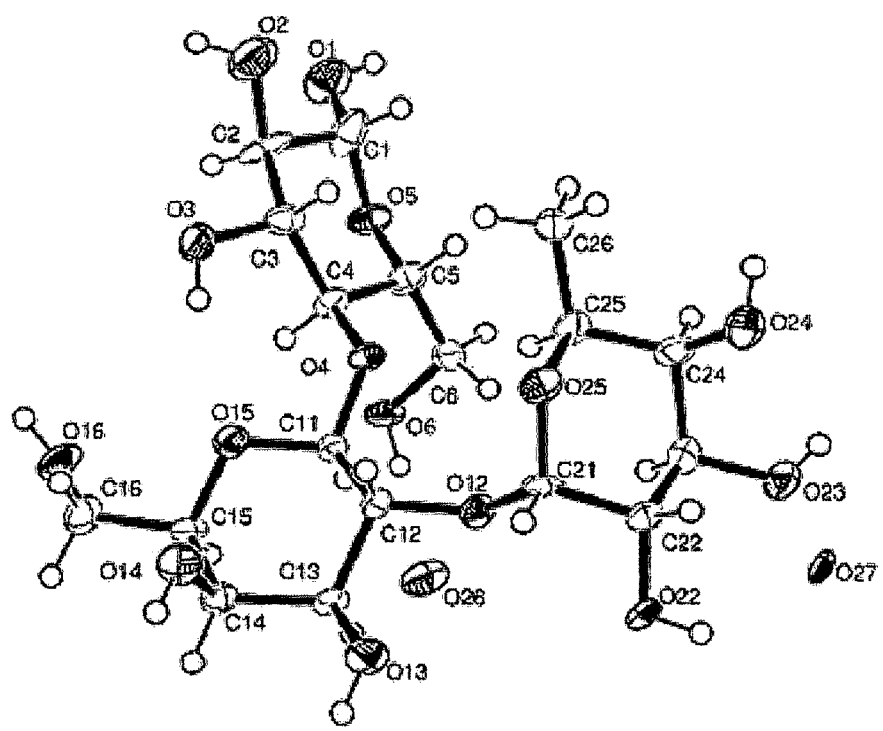
FIG. 5 Shows the ORTEP diagram of the single crystal structure of the 2'-O-Fucosyllactose Polymorph A of Example 2

Polymorph A obtained, surprisingly, in the solid state, presents itself exclusively in β anomeric form as shown by the single crystal structure (See FIG. 5). The anomeric percentage was also determined from the $^1$HNMR spectrum recorded in deuterated solvent at dissolution (See details in the experimental section). The spectra recorded in these conditions show a percentage of α anomer of less than 15%, preferably less than 10%.

The polymorph that is obtained can reach very high purity, with total impurities of less than 5%, preferably less than 3%, more preferably less than 1%, still more preferably less than 0.5%. Residual impurities can be small percentages of residual solvents, simple sugars (lactose, galactose, glucose, fucose), reaction intermediates, unreacted intermediates, and products of secondary reactions depending on the synthesis route employed.

To obtain Polymorph A, the 2'FL (amorphous, as a crystal or already in solution) is prepared as an aqueous solution at a concentration by weight between 53% and 75% and then charged with solvent.

Even more preferably, for the purposes of this invention and this description, the 2'-O-fucosyllactose is that in solution coming directly from the hydrogenation reaction, the final step of the synthesis as shown in WO2010/070616, which is brought to a concentration by weight of between 53% and 75% and then charged with the solvent, as mentioned above for obtaining Polymorph A.

The preferred concentration of the aqueous solution is between 60 and 65% by weight, and to this is added the solvent which can be absolute or have a variable water content, of up to 20%, preferably up to 15%, still more preferably up to 10%, and even more preferably up to 4%.

In the production of Polymorph A one of the methods involves concentrating 2'-O-Fucosyllactose to a syrup, maintaining the solution warm between 35 and 70° C., preferably between 45 and 67° C., still more preferably between 50 and 60° C., and additing the solvent warm or at boiling temperature. The solvent is added gradually and the mixture is left under agitation warm for between 1 and 15 hours. Then the mixture is allowed to return spontaneously to a temperature between 13 and 28° C., preferably between 20 and 25° C., filtered, washed with a water/solvent mixture, and the obtained solid dried.

The crystallisation mixture is maintained, during the addition of the solvent, at a temperature between 35 and 70° C., preferably between 45 and 67° C., still more preferably between 50 and 60° C. Typically one can observe the formation of a few crystallisation nuclei during or at the end of the addition of the solvent. Alternatively, the crystallisation can be initiated with a small quantity of crystals of Polymorph A.

The crystallisation mixture after the addition of the solvent, is maintained for 1-24 hours, preferably for 1-16 hours, still more preferably for 2-8 hours, at a temperature between 40 and 70° C., preferably between 45 and 67° C., and even more preferably between 55 and 65° C. Then the mixture is cooled or allowed to cool to room temperature in 1-24 hours. The mixture is maintained at room temperature (20-25° C.) for a time ranging from a few hours to a few days, preferably between 1 and 24 hours, still more preferably between 8 and 18 hours. Optionally the mixture, before being filtered to collect the crystalline solid, may be cooled further to 2-18° C., preferably to 5-15° C.

The operations for collecting the crystalline solid are those well known to experts in the field with usual means of filtration and suitable washing with aliquots of the water/solvent system used for crystallisation.

This invention also provides a method for preparing Polymorph A starting from Polymorph B. This phase change is made possible by drying Polymorph B in a desiccator with anhydrous silica gel for 12-48 hours, preferably 18-36 hours. Even more preferably drying can be conducted at 46-65° C., preferably at 48-55° C. at ambient pressure or lower and subsequent cooling to room temperature. With the latter procedure, Polymorph B, before transforming into A passes through a new anhydrous phase with characteristic XRPD peaks at 9.96±0.20, 18.88±0.20, 1.17±0.20, 11.79±0.2, 16.09±0.20, 12.62±0.2, 15.70±0.2, 14.20±0.2 2θ.

Polymorph A exhibits characteristic IR peaks at 3338±4 cm$^{-1}$, 2938±4 cm$^{-1}$, 1655±4 cm$^{-1}$, 1344±4 cm$^{-1}$, 1021±4 cm$^{-1}$, 819±4 cm$^{-1}$, 760±4 cm$^{-1}$, preferably at 3338±4 cm$^{-1}$, 2938±4 cm$^{-1}$, 1655±4 cm$^{-1}$, 1344±4 cm$^{-1}$, 1237±4 cm$^{-1}$, 1171±4 cm$^{-1}$, 1131±4 cm$^{-1}$, 1021±4 cm$^{-1}$, 819±4 cm$^{-1}$, 760±4 cm$^{-1}$, 687±4 cm$^{-1}$. In particular the peak at 1655±4 cm$^{-1}$ is present, much more intense than in the anhydrous polymorphs.

Under DSC analysis it shows a trend characterised by three endothermic peaks. The first has the maximum peak at the temperature of 61±3° C., the second at 182±3° C. and the third at 247±3° C. The first peak is attributable to dehydration, the second one to melting, and the third one to the decomposition of the sample.

The loss on drying of Polymorph A, carried out with Method 1 (See experimental section), varies from 1.5% by weight to 3% by weight, preferably from 1.1% by weight to 2.5% by weight.

Polymorph A shows characteristic Karl-Fischer values between 4.0% and 6.0% by weight and preferably between 4.4% and 5.2% by weight.

In particular Polymorph A, was subjected to studies of stability both accelerated at 40°±2° C.; 75±5% RH and at 25°±2° C., 60±5% RH. From these studies it was observed that the sample tends to adsorb humidity immediately (1-3 months) showing, compared to the start, an increase in the KF value that remains constant over time.

Figure 7:
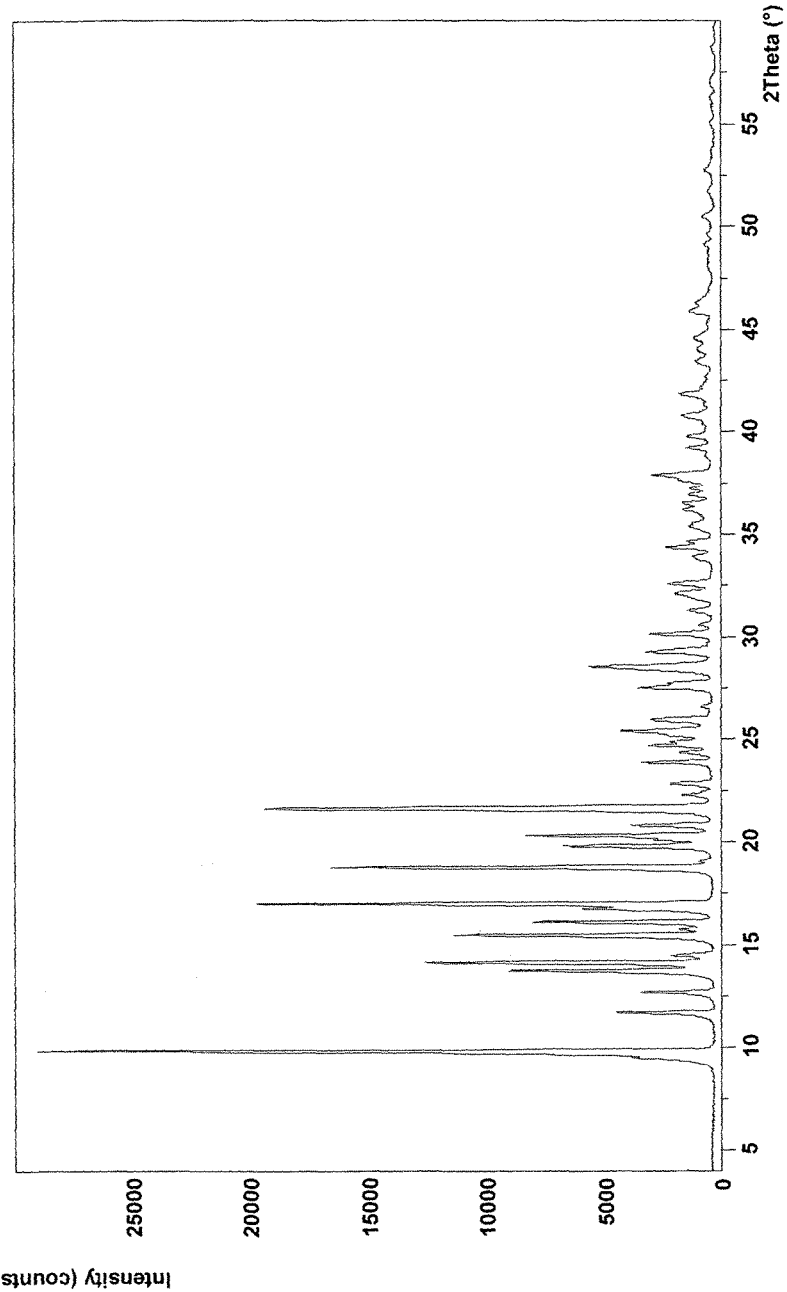
FIG. 7 Shows the X-ray powder diffraction spectrum of the 2'-O-Fucosyllactose Polymorph A of Example 4

In particular, the percentage of water takes values between 5% and 7%, preferably between 5.5% and 6.5%, still more preferably between 5.7% and 6.2% (See Table 1). This extra water detected by KF, however, is not crystallisation water because the XRPD spectrum of these samples continues to show the characteristic peaks of Polymorph A. What changes is the loss on drying which passes to values between 2.5% by weight to 4.8% by weight, preferably between 3.0% by weight to 4.3% by weight, and more preferably between 3.2% by weight and 4.0% by weight. See FIG. 7

TABLE 1 accelerated stability (40° ± 2° C. and 75 ± 5% RH) Polymorph A

| | Time (months) | | | | | |
|---|---|---|---|---|---|---|
| 0 | 1 | 2 | 3 | 4 | 5 | 6 |
| KF % 4.2 | 6.0 | 6.0 | 5.7 | 5.9 | 6.0 | 6.0 |

Polymorph A has characteristic XRPD peaks at 18.86±0.20, 9.89±0.20, 17.05±0.20 2θ, preferably at 18.86±0.20, 9.89±0.20, 17.05±0.20, 21.65±0.2, 14.20±0.20 2θ, more preferably at 18.86±0.20, 9.89±0.20, 17.05±0.20, 21.65±0.2, 14.20±0.20, 21.80±0.2, 16.17±0.2 2θ, still more preferably at 18.86±0.20, 9.89±0.20, 17.05±0.20, 21.65±0.2, 14.20±0.20, 21.80±0.2, 16.17±0.20, 20.36±0.2 2θ. The list of peaks with the relative intensities and the d (interplanar distances) of Polymorph A are shown in Table 2.

TABLE 2

List of XRPD peaks for Polymorph A

| Pos. [°2Th.] | d-spacing [Å] | Rel. Int. [%] |
|---|---|---|
| 9.5494 | 9.25416 | 16.40 |
| 9.8946 | 8.93207 | 87.81 |
| 11.7744 | 7.50996 | 31.79 |
| 12.7465 | 6.93932 | 26.09 |
| 13.8212 | 6.40205 | 21.77 |
| 14.2037 | 6.23051 | 58.63 |
| 14.5352 | 6.08914 | 14.69 |
| 15.5499 | 5.69399 | 31.30 |
| 15.8620 | 5.58265 | 5.89 |
| 16.1664 | 5.47824 | 49.80 |
| 16.8455 | 5.25888 | 23.05 |
| 17.0532 | 5.19528 | 78.13 |
| 18.8562 | 4.70239 | 100.00 |
| 19.8596 | 4.46702 | 12.50 |
| 20.1831 | 4.39615 | 14.08 |
| 20.3621 | 4.35790 | 42.32 |
| 20.8790 | 4.25116 | 11.55 |
| 21.6483 | 4.10181 | 74.01 |
| 21.7996 | 4.07366 | 54.07 |
| 22.2975 | 3.98382 | 3.66 |
| 22.9174 | 3.87744 | 4.57 |
| 23.9457 | 3.71322 | 14.66 |
| 24.4818 | 3.63310 | 6.05 |
| 24.7910 | 3.58848 | 16.98 |
| 24.9682 | 3.56342 | 10.54 |
| 25.5128 | 3.48857 | 14.14 |
| 25.9598 | 3.42950 | 5.68 |
| 26.1113 | 3.40996 | 5.77 |
| 26.6579 | 3.34126 | 2.62 |
| 27.5941 | 3.22999 | 12.98 |
| 28.6108 | 3.11747 | 15.62 |
| 29.3651 | 3.03909 | 12.50 |
| 30.1835 | 2.95853 | 9.56 |
| 30.6994 | 2.90998 | 1.15 |
| 31.4016 | 2.84649 | 1.86 |
| 32.1642 | 2.78072 | 6.24 |
| 32.6782 | 2.73814 | 5.35 |
| 33.8253 | 2.64787 | 2.14 |
| 34.0448 | 2.63129 | 3.35 |
| 34.4040 | 2.60464 | 7.45 |
| 34.6906 | 2.58377 | 4.41 |
| 35.3942 | 2.53400 | 2.66 |
| 36.3277 | 2.47100 | 4.54 |
| 36.5727 | 2.45501 | 5.22 |
| 37.0702 | 2.42319 | 3.37 |

Polymorph A as a single crystal has a spatial group of the type $P2_12_12_1$. It is arranged in an orthorhombic crystal system and the unit cell has the following parameters: a=12.4098(8) Å, b=12.737(2) Å, c=13.756(2) Å and a volume of 2212.5 Å$^3$.

The asymmetric unit of the crystal of the sample contains a molecule of 2'-O-Fucosyllactose and two sites containing water molecules. The site corresponding to the oxygen atom O26 (See FIG. 5) is fully occupied, whilst in the case of the site of the oxygen atom O27 the calculated occupancy is equal to 50%. From this we clearly see that the chemical composition of the crystal is such that for every molecule of polysaccharide there are 1.5 water molecules or 2'-O-fucosyllactose. $1.5H_2O$.

The single crystal X-ray analysis also shows that Polymorph A is present exclusively in β form (See FIG. 5).

This invention also relates to a method for preparing Polymorph B which is obtained by crystallisation from water. Crystallisation can be conducted with or without a primer.

Polymorph B is 2.5 hydrous and surprisingly occurs predominantly in β anomeric form, with an α anomer percentage less than 10%. The anomeric percentage is determined from the $^1$HNMR spectrum recorded in deuterated solvent at dissolution (See experimental section).

The polymorph obtained has a very high purity, greater than 95%, preferably greater than 97%, still more preferably greater than 99%. Impurities, depending on the method of obtaining 2'FL, may be residual solvents, simple sugars (lactose, galactose, glucose, fucose), reaction intermediates, unreacted intermediates, products of secondary reactions, 2'-O-Fucosyllactose in polymorphic form, or other amorphous phases (for example that of Polymorph A).

To obtain Polymorph B one of the methods involves concentrating it (or preparing an aqueous solution) to a weight percentage between 50 and 80%. Precipitation from the aqueous solution may optionally take place by seeding. The preferred concentration of the syrup is between 74% and 77% by weight.

In the production of Polymorph B one of the methods involves concentrating 2'FL to a syrup, maintaining it warm between 30 and 60° C., preferably between 35 and 50° C., more preferably between 38 and 48° C., still more preferably between 40 and 45° C. in the aqueous solution, and the optional addition of Polymorph B as seeding. At the end of concentration the syrup is kept hot for 1-12 hours, preferably for 1-8 hours, still more preferably for 1-4 hours. Typically one can observe the formation of crystals, or alternatively the crystallisation can be seeded with the addition of a small quantity of Polymorph B.

The crystallisation mixture is maintained at a temperature between 20 and 30° C., preferably between 20 and 25° C. for a time ranging from 10 hours to 10 days, preferably for about 12-120 hours, still more preferably for 12-24 hours.

The mixture is then cooled to between 2 and 18° C., preferably between 10 and 15° C. before collecting the crystal.

The crystal is filtered and washed with successive aliquots of water cooled to 4-15° C., preferably between 4 and 10° C.

Polymorph B shows characteristic IR peaks at 3340±4 cm$^{-1}$, 2938±4 cm$^{-1}$, 1655±4 cm$^{-1}$, 1348±4 cm$^{-1}$, 1023±4 cm$^{-1}$, 819±4 cm$^{-1}$, 762±4 cm$^{-1}$, preferably at 3340±cm$^{-1}$, 2938±cm$^{-1}$, 1655±4 cm$^{-1}$, 1348±4 cm$^{-1}$, 1239±4 cm$^{-1}$, 1173±4 cm$^{-1}$, 1133±4 cm$^{-1}$, 1023±4 cm$^{-1}$, 819±4 cm$^{-1}$, 760±4 cm$^{-1}$, 687±4 cm$^{-1}$. Even Polymorph B, as with Polymorph A, is distinguished from the anhydrous phases due to the presence of an intense peak at 1655±4 cm$^{-1}$.

The DSC analysis of Polymorph B shows three intense endothermic peaks, the first having the maximum peak at 83±3° C., the second at 182±3° C., and the third at 242±3° C. The first peak is attributable to dehydration, the second one to melting, and the third one to the decomposition of the sample.

Polymorph B is characterised by Karl-Fischer values of between 8.0% and 8.9% by weight, as well as losses on drying, measured by Method 1, between 5.2% by weight and 6.4% by weight.

Polymorph B has characteristic XRPD peaks at 9.96±0.20, 18.56±0.20, 20.48±0.20 2θ, preferably at 9.96±0.20, 18.56±0.20, 20.48±0.20, 14.21±0.20, 11.90±0.20 2θ, more preferably at 9.96±0.20, 18.56±0.20, 20.48±0.20, 14.21±0.20, 11.90±0.20, 19.84±0.2, 22.20±0.20 2θ, still more preferably at 9.96±0.20, 18.56±0.20, 20.48±0.20, 14.21±0.20, 11.90±0.20, 19.84±0.2, 22.20±0.20, 16.79±0.20, 2θ. The list of peaks with relative intensities and the d (interplanar distances) of Polymorph B are shown in Table 3.

TABLE 3

List of XRPD peaks for Polymorph B

| Pos. [°2Th.] | d-spacing [Å] | Rel. Int. [%] |
|---|---|---|
| 9.1778 | 9.62805 | 25.75 |
| 9.2632 | 9.53951 | 25.64 |
| 9.9612 | 8.87255 | 100.00 |
| 11.6236 | 7.60706 | 19.71 |
| 11.9041 | 7.42844 | 43.84 |
| 13.8934 | 6.36897 | 16.00 |
| 14.0269 | 6.30864 | 37.88 |
| 14.2108 | 6.22742 | 47.68 |
| 15.1931 | 5.82692 | 8.30 |
| 15.5341 | 5.69975 | 34.04 |
| 15.8480 | 5.58757 | 35.04 |
| 16.7859 | 5.27742 | 39.87 |
| 18.5609 | 4.77655 | 85.09 |
| 19.6786 | 4.50770 | 18.05 |
| 19.8445 | 4.47039 | 43.36 |
| 20.4789 | 4.33330 | 47.79 |
| 20.8612 | 4.25475 | 20.12 |
| 21.6447 | 4.10248 | 8.12 |
| 22.1968 | 4.00166 | 41.97 |
| 22.7019 | 3.91376 | 9.34 |
| 22.9013 | 3.88014 | 13.27 |
| 23.3036 | 3.81406 | 15.83 |
| 23.9677 | 3.70985 | 16.31 |
| 24.5568 | 3.62217 | 16.76 |
| 25.5249 | 3.48695 | 11.44 |
| 25.9384 | 3.43228 | 19.42 |
| 26.3721 | 3.37682 | 4.65 |
| 27.0745 | 3.29079 | 2.96 |
| 28.0196 | 3.18190 | 12.44 |
| 28.8292 | 3.09436 | 15.78 |
| 29.2610 | 3.04966 | 11.39 |
| 29.7297 | 3.00265 | 5.36 |
| 30.1664 | 2.96017 | 3.63 |
| 30.8471 | 2.89638 | 2.04 |
| 31.4947 | 2.83829 | 5.55 |
| 31.6945 | 2.82085 | 9.83 |

The unit cell obtained from the single crystal collection of Polymorph B is orthorhombic (a=14.762, b=12.622, c=12.3540) and perfectly in accordance with that calculated from the powder spectrum (a=14.905 (7), b=12.663 (6), c=12.447 (5)). The spatial group in which it crystallises is P2$_1$2$_1$2$_1$ and it has a cell volume of 2349.4 Å$^3$ against the 2212.5 Å$^3$ of Polymorph A.

This invention also relates to a method for preparing Polymorph C.

Said polymorph is obtained by crystallisation with alcohols or mixtures thereof. The preferred alcohols are C1 and C3 alcohols and crystallisation is conducted without seeding.

Polymorph C is anhydrous; the weight loss on drying corresponds to small quantities of water and/or residual solvents in the sample.

In particular, the residual water content is less than 1.0% by weight, preferably less than 0.4% by weight, and in particular less than 0.3% by weight. The content of any residual solvents is less than 1.3% by weight, preferably less than 0.8% by weight, still more preferably less than 0.3% by weight.

Polymorph C is unexpectedly in 3 anomeric form with a percentage of a anomer less than 15%, preferably less than 10%. The anomeric percentage is determined from the $^1$HNMR spectrum recorded in deuterated solvent at dissolution (See experimental section).

The polymorph obtained has a high purity, greater than 95%, preferably greater than 97%, still more preferably greater than 99%. Any impurities present may be, depending on the obtainment method, residual solvents, simple sugars (lactose, galactose, glucose, fucose), reaction intermediates, unreacted intermediates, products of secondary reactions, 2'-O-Fucosyllactose in amorphous form, or other polymorphic phases.

In the production of Polymorph C one of the methods involves the concentration of 2'-O-fucosyllactose to an amorphous solid and its solubilisation in C1-C4 alcohol or mixtures thereof.

The alcohol solution, preferably methanol, is kept hot at a temperature between 30 and 50° C., preferably between 40 and 45° C.

The mixture is kept hot for 1-16 hours, preferably 1-8 hours, still more preferably 1-4 hours, during which one can observe the formation of crystals. The mixture is cooled to 10-25° C., preferably 10-15° C. in 2-20 hours, and then the solid is filtered and washed with aliquots of crystallisation solvents.

Alternatively to the previous method, Polymorph C is also obtained by the phase transformation of Polymorph A.

In particular Polymorph A is suspended in a C1-C3 alcohol or mixture thereof and the mixture is warmed to a temperature between 30 and 70° C., preferably between 45 and 67° C., still more preferably between 60 and 65° C.

The crystallisation mixture is kept warm for 1-24 hours, preferably 1-12 hours, more preferably 1-8 hours, still more preferably 1-4 hours. Whilst maintaining warm one can observe an increase in crystals in suspension.

The mixture is cooled or allowed to cool to ambient temperature and, optionally, before being filtered to collect the crystalline solid, may be cooled further to a temperature between 10 and 15° C.

The operations for collecting the crystalline solid are those well known to experts in the field with usual means of filtration and suitable washing with aliquots of the solvents used for crystallisation.

Polymorph C has characteristic IR peaks at 3403±4 cm$^{-1}$, 2931±4 cm$^{-1}$, 1425±4 cm$^{-1}$, 1149±4 cm$^{-1}$, 1075±4 cm$^{-1}$, 765±4 cm$^{-1}$, preferably at 3403±4 cm$^{-1}$, 2931±4 cm$^{-1}$, 1425±4 cm$^{-1}$, 1369±4 cm$^{-1}$, 1306±4 cm$^{-1}$, 1149±4 cm$^{-1}$, 1076±4 cm$^{-1}$, 965±4 cm$^{-1}$, 818±4 cm$^{-1}$, 765±4 cm$^{-1}$.

The DSC analysis of the crystalline phase C shows a single endothermic peak at 223±3° C., preferably at 223±2° C.

The crystals of Polymorph C present a Karl-Fischer value of between 2.0% and 0.1% by weight, preferably between 1.0% and 0.2% by weight and the residual solvent, calculated with $^1$HNMR, is between 2.0% and 0.1% by weight, preferably between 1.0% and 0.3% by weight.

The loss on drying of this crystalline phase is between 4.0% and 0.2%, preferably between 2.0% and 0.5% by weight, more preferably between 1.5% and 1.0% by weight.

Polymorph C has characteristic XRPD peaks at 17.58±0.20, 17.44±0.20, 10.63±0.20 2θ, preferably at 17.58±0.20, 17.44±0.20, 10.63±0.20, 5.30±0.2, 20.05±0.20, 2θ, more preferably at 17.58±0.20, 17.44±0.20, 10.63±0.20, 5.30±0.2, 20.05±0.20, 18.91±0.2, 21.00±0.2 2θ, still more preferably at 17.58±0.20, 17.44±0.20, 10.63±0.20, 5.30±0.2, 20.05±0.20, 18.91±0.2, 21.00±0.2, 22.81±0.20 2θ. The list of peaks with the relative intensities and the d (interplanar distances) of Polymorph C are shown in Table 4.

The unit cell obtained from the powder spectrum is of the monoclinic type (a=5.058(1), b=12.773(3), c=16.692(5); α=90, β=94.743(8), γ=90) and has a volume of 1074.75 Å$^3$ much lower than the hydrous types.

TABLE 4

List of XRPD peaks for Polymorph C

| Pos. [°2Th.] | d-spacing [Å] | Rel. Int. [%] |
|---|---|---|
| 5.2986 | 16.66498 | 54.15 |
| 8.7229 | 10.12909 | 19.13 |
| 10.6310 | 8.31501 | 67.15 |
| 12.6930 | 6.96843 | 22.76 |
| 13.8592 | 6.38458 | 10.40 |
| 14.8516 | 5.96012 | 7.10 |
| 15.9762 | 5.54303 | 27.26 |
| 17.4366 | 5.08193 | 77.38 |
| 17.5847 | 5.03946 | 100.00 |
| 17.9325 | 4.94249 | 6.30 |
| 18.9093 | 4.68931 | 36.51 |
| 19.2480 | 4.60756 | 26.99 |
| 19.8104 | 4.47799 | 18.56 |
| 20.0522 | 4.42454 | 41.44 |
| 21.0022 | 4.22651 | 32.45 |
| 22.4667 | 3.95420 | 19.02 |
| 22.8106 | 3.89535 | 27.46 |
| 23.4467 | 3.79109 | 4.97 |

This invention also relates to an alternative method for obtaining Polymorph I, previously described in WO2011/150939; particularly further subject-matter of the invention is a method for preparing Polymorph I, said method comprising crystallisation from glacial acetic acid.

Polymorph I, according to this method can be obtained, starting from Polymorph A or B or from the amorphous form of 2'FL, by treatment with glacial acetic acid at 60-80° C. Crystallisation occurs, preferably, without a seeding.

Polymorph I, as described in patent WO2011/150939, is obtained predominantly in α anomeric form. The anomeric percentage is determined from the $^1$HNMR spectrum recorded in deuterated solvent at dissolution (See experimental section). The crystallisation mixture is kept warm in 10-20 volumes of glacial acetic acid for 1-10 hours, and then allowed to cool to room temperature. Optionally the mixture, before being filtered to collect the crystalline solid, can be further cooled to 12-15° C.

The operations for collecting the crystalline solid are those well known to experts in the field with usual means of filtration and suitable washing with aliquots of the solvent used for crystallisation.

A further subject-matter of this invention is a Polymorph A, B or C as described above for use as a medicament, as a dietary supplement, or an ingredient in cosmetics.

The scope of the invention therefore also includes pharmaceutical, food, or cosmetics compositions comprising any one of Polymorphs A, B or C as described above. Particularly preferred food compositions are infant formulas. This invention will be better understood in light of the following embodiments.

Experimental Section

Analytical Methods:
1) DSC Analysis

The differential calorimetric analyses were carried out using a Mettler T STAR$^e$ system instrument (Mettler Toledo, Switzerland) equipped with a DSC cell. Samples weighed with a Mettler MX5 microbalance in suitable A1 containers, subsequently sealed and perforated, underwent analysis, carried out at a scan rate of 10° C./min in the temperature range 30 to 300° C. in static air.

The instrument was previously calibrated with indium as a standard (purity 99.98%, melting point 156.61° C., melting enthalpy 28.71 J/g).

2) Karl-Fischer Analysis

Determination of water content in the product based on a specific oxidation-reduction reaction between the water present in the sample and the Karl Fischer reagent.

List of Equipment and Reagents

Metrohm automatic titrator mod. 701KF Titrino.
Analytical balance
Hydranal composite 2 Riedel de Haen or equivalent
Hydranal solvent Riedel de Haen or equivalent
Modes of Operation
The parameters used are as follows:

| | |
|---|---|
| I(pol) | 12 µA |
| EP | 250 mV |
| Stop crit. | Drift |
| Drift | 20 µl/min |
| Max rate | 30 mL/min |
| Min. volume incr. | 9µ |

About 200 mg of the 2'-FL were weighed into the appropriate container, the balance was set to zero and the substance transferred into the previously dehydrated cell. The empty container was placed on the pan of the balance to determine the exact value of the substance transferred into the cell. Set the measured weight into the formula:

$$\% H_2O = V \times T \times F / PC$$

Where:
V=volume of Karl Fischer reagent used at the equivalent point;
T=Titre of the reagent in mg/mL;
PC=Weight of the sample analysed;
F=multiplication factor=100.

The table below shows the theoretical percentages by weight of water compared to the degree of hydration of the molecule.

| Type | 2'FL•1H$_2$O | 2'FL•1.5H$_2$O | 2'FL•2H$_2$O | 2'FL•2.5H$_2$O | 2'FL•3H$_2$O |
|---|---|---|---|---|---|
| % H$_2$O (p/p) | 3.6 | 5.2 | 6.9 | 8.4 | 10 |

3) LOD

Gravimetric method with heating of the sample using a halogen lamp Ohaus themobalance mod. 45 MB
Method 1
The conditions of Method 1 are as follows:
Profile: phases
Step 1: 50° C. for 1 minute
Step 2: 60° C. for 1 minute
Final: 90° C.
Power off: alib (<1 mg in 120 seconds)
Unit. Per.: OFF
Target weight: none
Method 2

The conditions of Method 2 are as follows:
Profile: phases
Step 1: 50° C. for 1 minute
Step 2: 50° C. for 1 minute
Final: drying temperature 56° C.
Power off: alib (<1 mg in 60 seconds)
Unit. Per.: OFF
Target weight: none 4) $^1$HNMR Analyses The $^1$HNMR analyses were carried out on a Varian VXR300 or Gemini 200 dissolving 10 mg of product in 0.75 ml of D$_2$O or DMSO in a tube for NMR spectra. The spectra were recorded at dissolution and at equilibrium.

In the first case the tube is prepared with the product and deuterated solvent and the spectrum immediately recorded.

In the second case the product is dissolved in deuterated solvent, left to equilibrate at least one night, and then the spectrum is recorded.

For the spectra in D$_2$O, in order to calculate the a/β ratio, reference is made to the following peaks:
  a) peak at 5.3 ppm (H-1 fucose)
  b) peak at 5.2 ppm (H-1 α glucose)

The calculation of the percentage of α compared to β is as follows:

(Integral of signal b/Integral of signal)*100

For the spectra in DMSO reference is made to the following peaks:
  c) peak at 6.7 ppm (OH glucose β)
  d) peak at 6.3 ppm (OH glucose α)

The calculation of the percentage of a compared to β is as follows:

[Integral of signal d/(integral of signal c+integral of signal d)]*100

5) Melting Point

The melting point analyses were carried out with a BUCHI Melting Point B-540.

An aliquot of the solid is placed into a melting point capillary tube and inserted into the appropriate slot on the instrument. A preliminary analysis is carried out with fast heating to check the approximate melting temperature. The analysis is then repeated by setting a rapid heating to 10-15° C. below the melting temperature and then a heating of 2° C./minute until the melting/decomposition of the sample is observed.

6) Powder Spectra

An aliquot of the substance, between 10 and 20 mg was ground and placed on a zero-background sample holder. For each sample, spectra were recorded on an X'PERT PRO diffractometer with Cu-Kα radiation (λ=1.5418) in the range 2θ 4-60°.

Spectra at various temperatures have been recorded with the same instruments.

In situ thermodiffractometry was carried out in an Anton Paar HTK1200N high-temperature chamber. Powder spectra were recorded at the temperatures 25, 50, 75, 100, 125 and 150° C. with a heating ramp of 5° C./min. Similarly the spectra were recorded at 125, 100, 75, 50, 25° C. whilst cooling.

7) X-Ray

The data were collected at 100K using an Oxford Diffraction Xcalibur 3 diffractometer equipped with Cu-Kα radiation and a CCD detector. Data were collected using the CrysAlis CCD programme whilst the data reduction was carried out with the CrysAlis CCD programme. Absorption correction was applied with the ABSPACK programme. The structure was solved by direct methods using the SIR97 programme and refined through the F2s with the full-matrix least-squares techniques with the SHELXL programme. All atoms excepting hydrogen atoms were refined anisotropically. The hydrogen atoms bonded to the carbon atoms and the hydroxyl groups were placed in calculated positions and with an isotropic factor of 20% or 50% greater than that of the atoms to which they are bonded.

8) TGA and DTA

Thermogravimetric analysis (TGA) and the coupled differential thermal analysis (DTA) were carried out on a Seiko EXSTAR 6200 Thermogravimetric Analyser (TGA/DTA) under a flow of nitrogen (50 mL/min) with a heating ramp of 5° C. min$^{-1}$ 9) IR Determination Equipment Used Perkin Elmer IR mod. BX2

Modes of Operation

In an agate mortar, a mixture made up of 1 to 2 mg of product and 100 to 150 mg of infrared grade KBr previously dried at 105° C. overnight, is ground thoroughly. The mixture is transferred into the appropriate holder and maintained under vacuum and under a pressure of 100 Kg/m$^2$ (10 Tons/ft$^2$) for at least 30 minutes. The spectrum is recorded in the range 4000+600 cm$^{-1}$

10) HPLC

The HPLC analyses are undertaken for comparison with a standard weighed with the following equipment:

HPLC line with thermostated cell refractive index detector, isocratic pump and autosampler.

300 mm long stainless steel column filled with Transgenomic IC-SEP ICE-ION-300 stationary phase (Stepbio cod. ICE-99-9850) equipped with a similar guard cartridge (code ICE-99-2364).

Column temperature: 45° C.

Injections: 20 µl.

Flow: 0.4 mL/minute.

Integrator: Perkin Elmer Totalchrom workstation

The experimental section shows examples where the starting fucosyllactose was obtained as described in patent WO2010/070616 for which below is the scheme of the synthesis and the last step in detail:

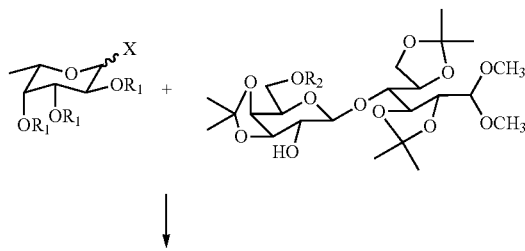

-continued

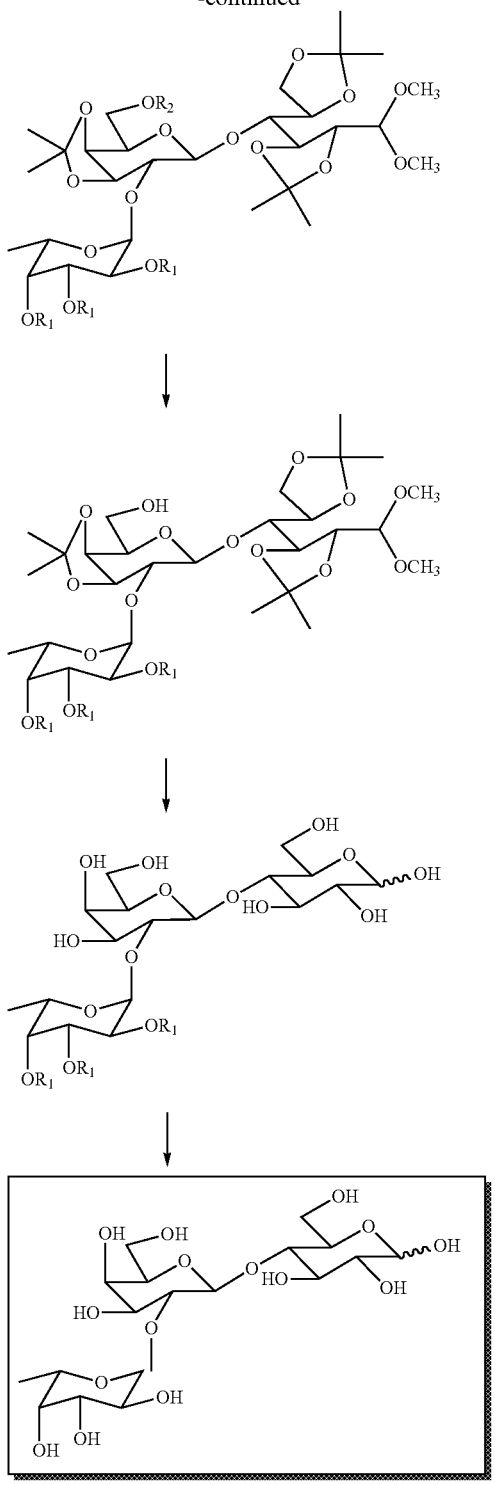

R₁ = benzyl groups substituted with chlorine, bromine, alkoxy, or nitro groups
R₂ = a group selected from acryl, alkyl, or aryl, benzyl, P, trityl, silyl-derived; preferably R3 is acyl, and more preferably acetyl or benzoyl, optionally mono- or di-, substituted by chlorine, bromine, alkoxy, or nitro groups.

65.00 g of O-[2,3,4-Tri-O-(4-Chlorobenzyl)-6-Deoxy-α-L-Galactopyranosyl]-(1→2)-O-β-D-Galactopyranosyl-(1→4)-D-Glucose, 20 g of sodium acetate, 9.3 g of unreduced 5% Pd/C, and 880 g of methanol were loaded into a reactor. The solution, kept under agitation, after 3 cycles of vacuum/nitrogen, had hydrogen blown into it up to 1.5 bar. The mixture was heated to 60° C. in 3 hours and maintained at temperature at 1.8 bar for 16 hours. The TLC control (Toluene, methanol, AcOH 10:10:1) shows that the reaction is complete.

The suspension was then filtered over dicalite, concentrated to a syrup and reconstituted with 150 mL of demineralised water. The aqueous solution was extracted with ethyl acetate (3×30 ml), concentrated to 20-25° Brix and deionised on a pair of ion exchange resins (IR 120(H⁺) and FPA 55).

In the product obtained after deionisation, there is an impurity, 2'-Fucosyllactose methyl glycoside, in a variable percentage up to 5%.

The solution of 2'-O-fucosyllactose thus obtained can be brought to a certain saccharometric concentration in order to be crystallised or dried in a vacuum (80 mbar) and hot (50° C.) to produce an amorphous solid.

Polymorph A

Example 1

24 Kg of 2'FL are brought to a concentration of 64° Brix and heated to 55-60° C. Over the period of 70 minutes, 112 L of 96% ethanol were added, maintaining the temperature at 45±10° C. The mixture, mid-addition, self-primed at 37° C. The suspension was left under agitation for 4 hours at 55° C. and was then brought to room temperature in 13 hours. After about 72 hours under agitation at room temperature it was cooled to 10° C. in 3 hours. The solid was filtered, washed with 1 volume of water/ethanol=9/1 and dried under vacuum at 60° C. for 10 hours and then one night in static vacuum without heating.

Figure 1:
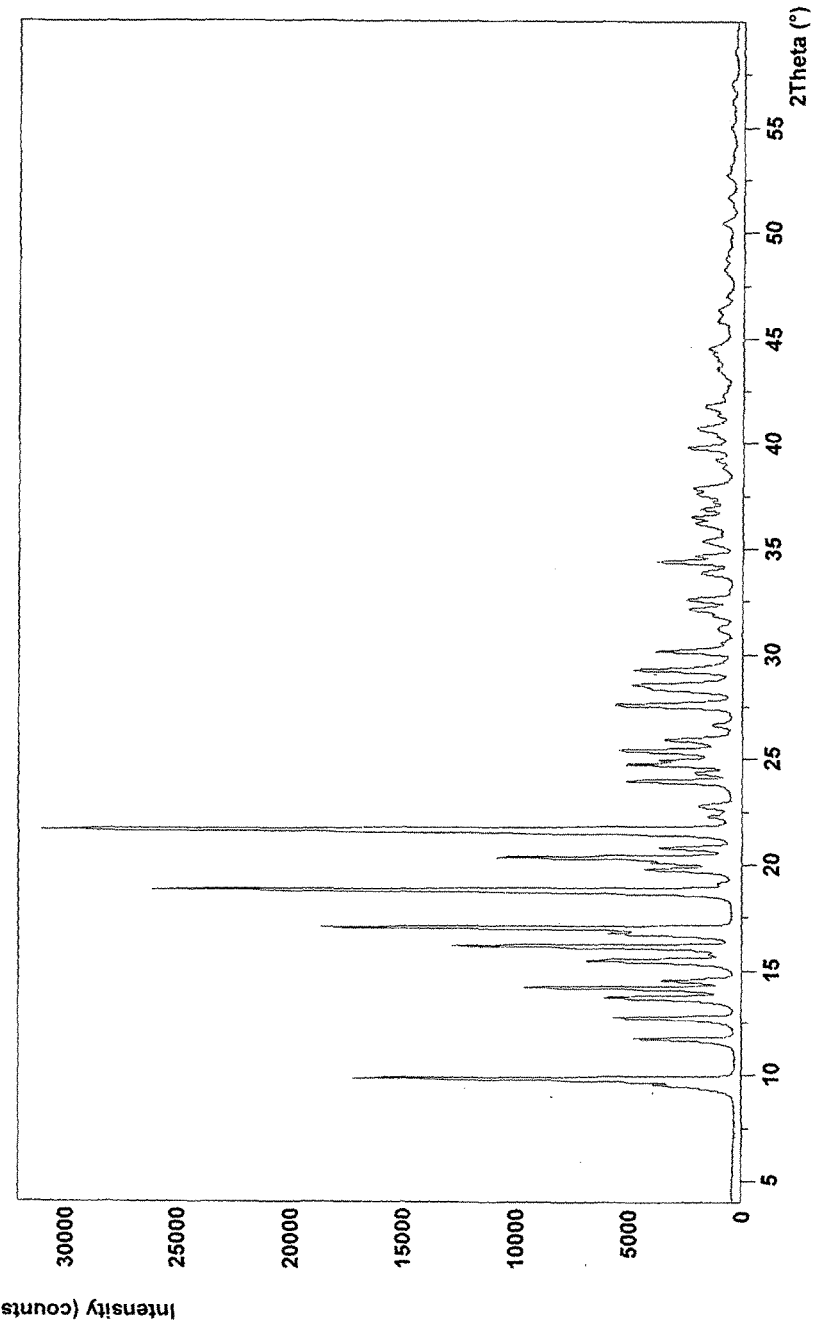
FIG. 1 Shows the X-ray powder diffraction spectrum of the 2'-O-Fucosyllactose Polymorph A of Example 1

The solid obtained (20.7 Kg dry) presents:
KF=5.0%;
LOD=1.98% (Method 1)
PF=177-186
¹HNMR (D₂O) at dissolution (300 MHz; nt=1): α anomer/β anomer=10/90;
Powder diffraction spectrum=Shows the phase of Polymorph A (2'FL.1.5H₂O) (See FIG. 1)

Example 2

50 measured Kg of 2'FL were brought to a concentration of 630 Brix. The internal temperature was increased and maintained at 55° C. during the addition of 222 L of 96% ethanol (35 minutes). The mixture was seeded with 200 g of Polymorph A and maintained, after crystallisation occurred, for 6 hours at 56° C., then brought down to 25° C. in 4 hours. The suspension, after 18 hours at 23° C., was cooled to 11° C. in 3 hours and then filtered. The solid was washed with 1.5 volumes of ethanol/water mixture=9/1.

Figure 2:
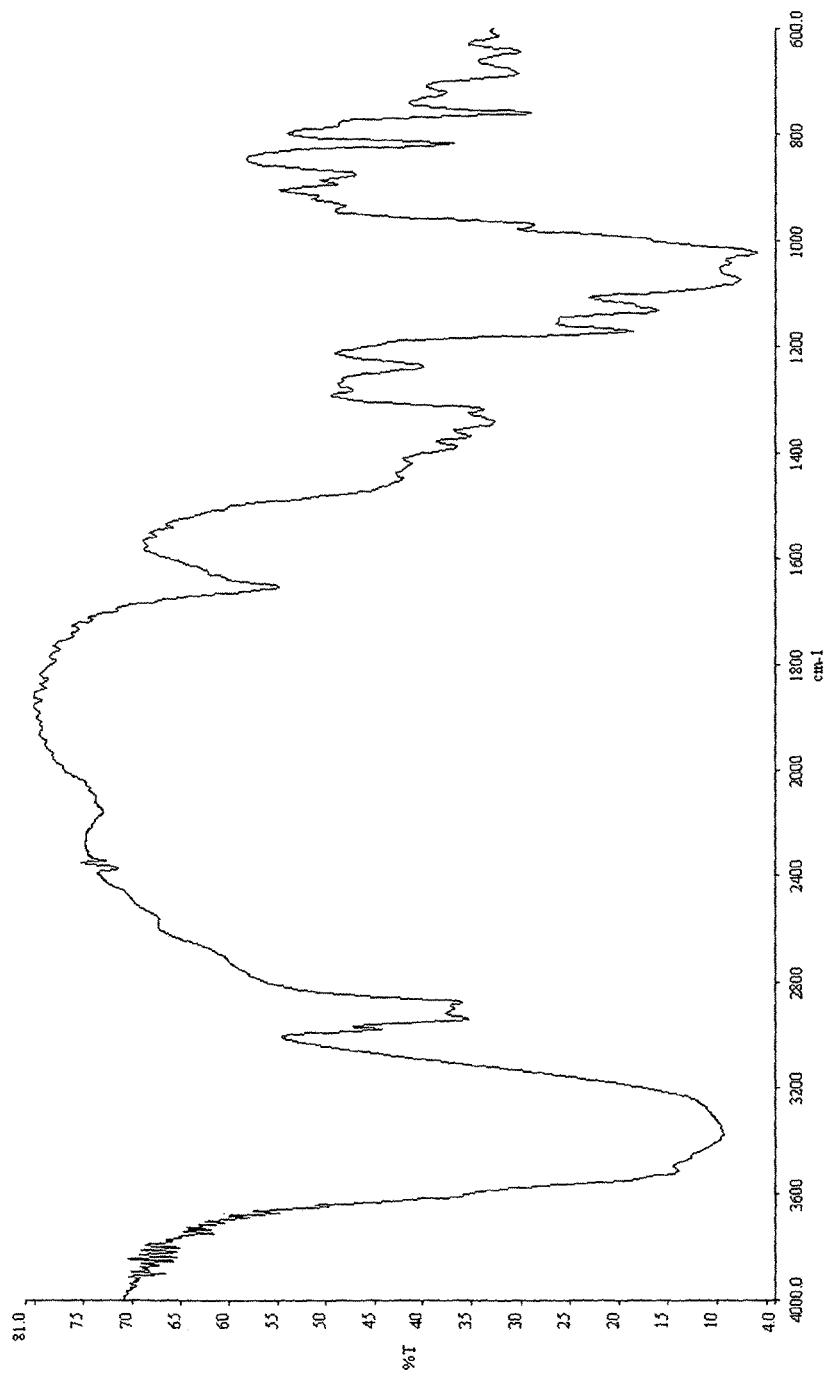
FIG. 2 Shows the IR spectrum of the 2'-O-Fucosyllactose Polymorph A of Example 2
Figure 3:
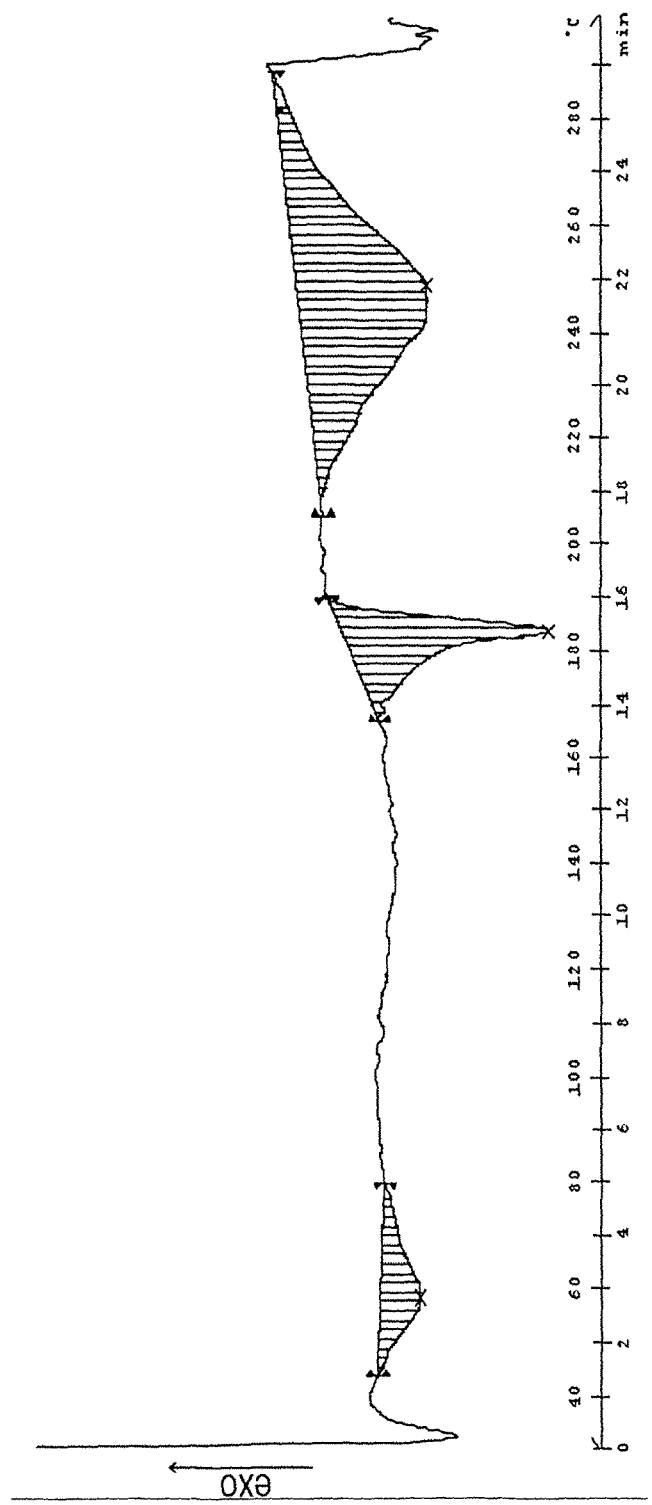
FIG. 3 Shows the differential scanning calorimetry analysis curve of the 2'-O-Fucosyllactose Polymorph A of Example 2

After drying in a vacuum at 60° C., 49.5 kg of dry solid were obtained.
KF=4.54%
LOD=0.73% (Method 2); 1.86% (Method 1)
PF=175-184° C.
¹HNMR (D₂O) at dissolution (300 MHz; nt=1): α anomer/β anomer=13/87
IR=3337, 9; 2978, 44; 2938, 35; 1655, 55; 1388, 36; 1342, 33; 1237, 40; 1171, 19; 1132, 16; 1072, 8; 1023, 6; 877, 47; 818, 37; 760, 29; 722, 38; 686, 30; 644, 30. (See FIG. 2)
DSC=Initial broadened endothermic effect, ranging between 45 and 85° C., desolvation phenomena index, followed by an intense endothermic peak ($T_{onset}$=178.10° C.; $T_{peak}$=184.68) attributable to the melting of the sample, followed, at higher temperatures by an intense endothermic band with a peak at 247.8° C. due to phenomena of thermal decomposition. (See FIG. 3)

Figure 4:
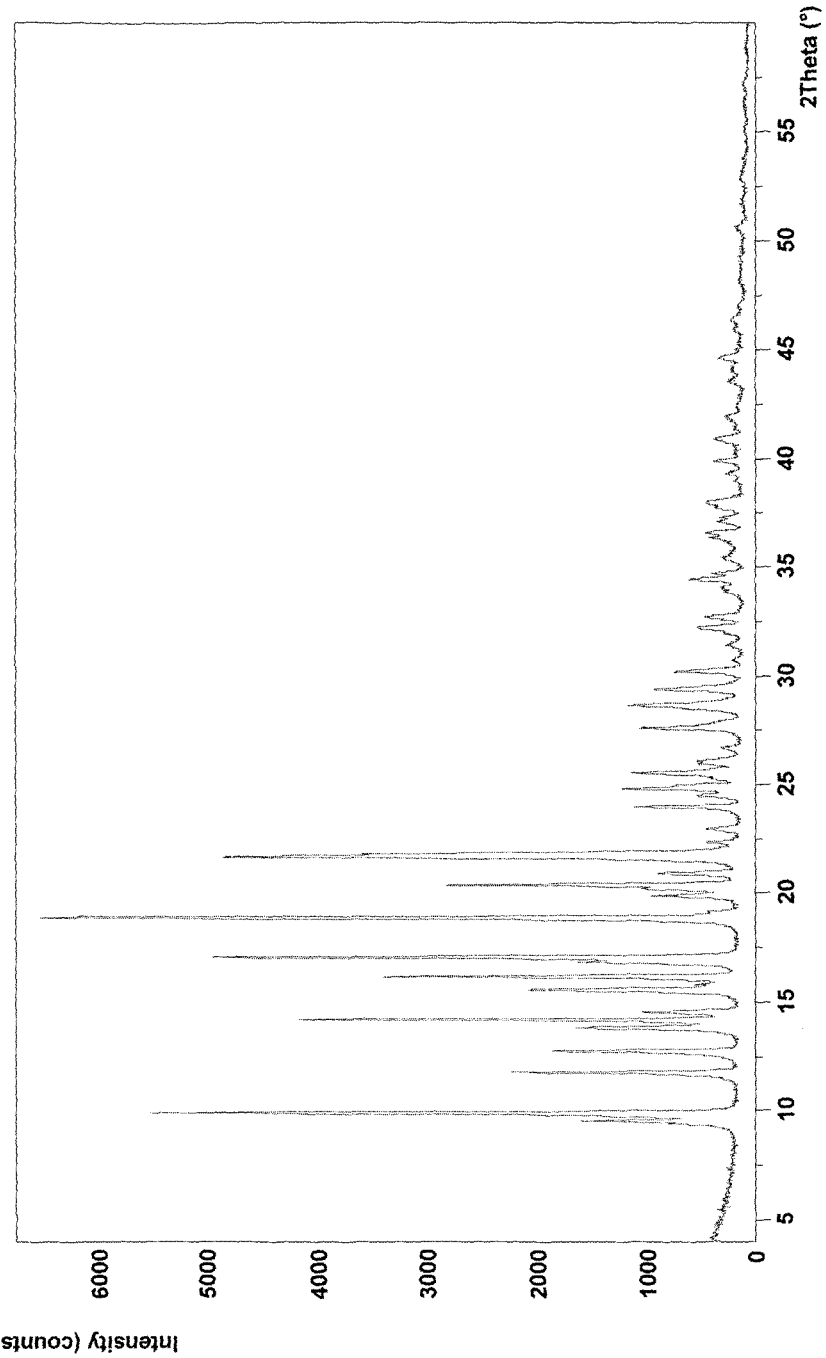
FIG. 4 Shows the X-ray powder diffraction spectrum of the 2'-O-Fucosyllactose Polymorph A of Example 2

Powder XRPD spectrum=Shows the phase of Polymorph A (2'FL.3/2H$_2$O). See FIG. 4 Single crystal refinement XRD:

TABLE 5

Crystallographic data and details of structure refinement

| | |
|---|---|
| Empirical formula | 2x(C$_{18}$H$_{32}$O$_{15}$) 3xH$_2$O |
| Formula weight | 1030.92 |
| Temperature | 100(2) K |
| Wavelength | 1.54184 Å |
| Crystal system | Orthorhombic |
| Space group | P 2$_1$ 2$_1$ 2$_1$ |
| Unit cell dimensions | a = 12.4098(8) Å |
| | b = 12.737(2) Å |
| | c = 13.756(2) Å |
| Volume | 2174.3(5) Å$^3$ |
| Z | 2 |
| Density (calculated) | 1.575 Mg/m$^3$ |
| Absorption coefficient | 1.225 mm$^{-1}$ |
| F(000) | 1100 |
| Crystal size | 0.1 × 0.05 × 0.05 mm$^3$ |
| Theta range for data collection | 4.73 to 70.96°. |
| Index ranges | −14 <= h <= 6, −10 <= k <= 15, −11 <= l <= 16 |
| Reflections collected | 6449 |
| Independent reflections | 3634 [R(int) = 0.0439] |
| Completeness to = 65° | 99% |
| Absorption correction | Semi-empirical from equivalents |
| Max. and min. transmission | 1 and 0.0916 |
| Refinement method | Full-matrix least-squares on F2 |
| Data/restraints/parameters | 3634/0/328 |
| Goodness-of-fit on F2 | 1.064 |
| Final R indices [I > 2(I)] | R$_1$ = 0.0726, wR$_2$ = 0.1779 |
| R indices (all data) | R$_1$ = 0.1082, wR$_2$ = 0.2124 |
| Extinction coefficient | 0.0069(8) |
| Largest diff. peak and hole | 0.855 and −0.436 e · Å$^{-3}$ |

The asymmetric unit of the crystal of the sample contains a molecule of 2'-O-fucosyllactose and two sites containing water molecules. The site corresponding to the oxygen atom O26 is fully occupied, whilst in the case of the site of the oxygen atom O27 we have a calculated occupancy of 50%. From this we clearly see that the chemical composition of the crystal is such that for every molecule of polysaccharide there are 1.5 water molecules or 2'-O-fucosyllactose.3/2H$_2$O (See FIG. 5). This ratio between water molecules and 2'-O-fucosyllactose is confirmed by thermogravimetry (TGA).

TABLE 6

Atomic co-ordinates

| | x | y | z | U(eq) |
|---|---|---|---|---|
| C(1) | 7641(5) | 3409(6) | −2842(8) | 43(2) |
| C(2) | 7757(5) | 2328(7) | −2411(7) | 43(2) |
| C(3) | 6657(5) | 1798(6) | −2310(5) | 28(2) |
| C(4) | 5842(4) | 2514(5) | −1839(6) | 24(2) |
| C(5) | 5850(4) | 3599(6) | −2253(6) | 27(2) |
| C(6) | 5086(5) | 4363(6) | −1763(5) | 29(2) |
| C(11) | 4238(4) | 1796(5) | −1154(5) | 21(1) |
| C(12) | 3157(4) | 1295(6) | −1416(2) | 23(2) |
| C(13) | 2594(4) | 985(6) | −480(5) | 23(2) |
| C(14) | 3317(5) | 307(5) | 184(5) | 23(2) |
| C(15) | 4417(4) | 841(6) | 301(5) | 22(2) |
| C(16) | 5211(5) | 191(6) | 869(6) | 32(2) |
| C(21) | 2073(4) | 1755(6) | −2811(5) | 24(2) |
| C(22) | 1256(5) | 2552(5) | −3149(5) | 26(2) |

TABLE 6-continued

Atomic co-ordinates

| | x | y | z | U(eq) |
|---|---|---|---|---|
| C(23) | 1782(5) | 3552(7) | −3511(6) | 36(2) |
| C(24) | 2681(5) | 3340(6) | −4229(6) | 30(2) |
| C(25) | 3440(4) | 2528(5) | −3806(5) | 28(2) |
| C(26) | 4320(5) | 2185(6) | −4481(5) | 32(2) |
| O(1) | 8611(4) | 3946(5) | −2815(5) | 47(2) |
| O(2) | 8367(4) | 1787(5) | −3161(4) | 49(2) |
| O(3) | 6800(3) | 848(4) | −1782(4) | 34(1) |
| O(4) | 4804(3) | 2021(4) | −2000(3) | 25(1) |
| O(5) | 6941(3) | 4006(6) | −2160(4) | 29(1) |
| O(6) | 5153(3) | 4320(4) | −724(3) | 29(1) |
| O(12) | 2532(3) | 2092(4) | −1917(3) | 24(1) |
| O(13) | 1622(3) | 422(4) | −726(4) | 31(1) |
| O(14) | 3498(4) | −703(4) | −226(4) | 32(1) |
| O(15) | 4864(3) | 1026(4) | −629(3) | 26(1) |
| O(16) | 6192(3) | 765(4) | 1053(4) | 39(1) |
| O(22) | 523(3) | 2793(4) | −2372(3) | 32(1) |
| O(23) | 983(4) | 4217(5) | −3929(5) | 55(2) |
| O(24) | 2165(3) | 2983(5) | −5099(4) | 37(1) |
| O(25) | 2850(3) | 1585(4) | −3536(4) | 27(1) |
| O(26) | 3115(4) | 3949(4) | −75(4) | 41(1) |
| O(27) | 367(5) | 5832(7) | −3078(7) | 24(2) |

Figure 6:
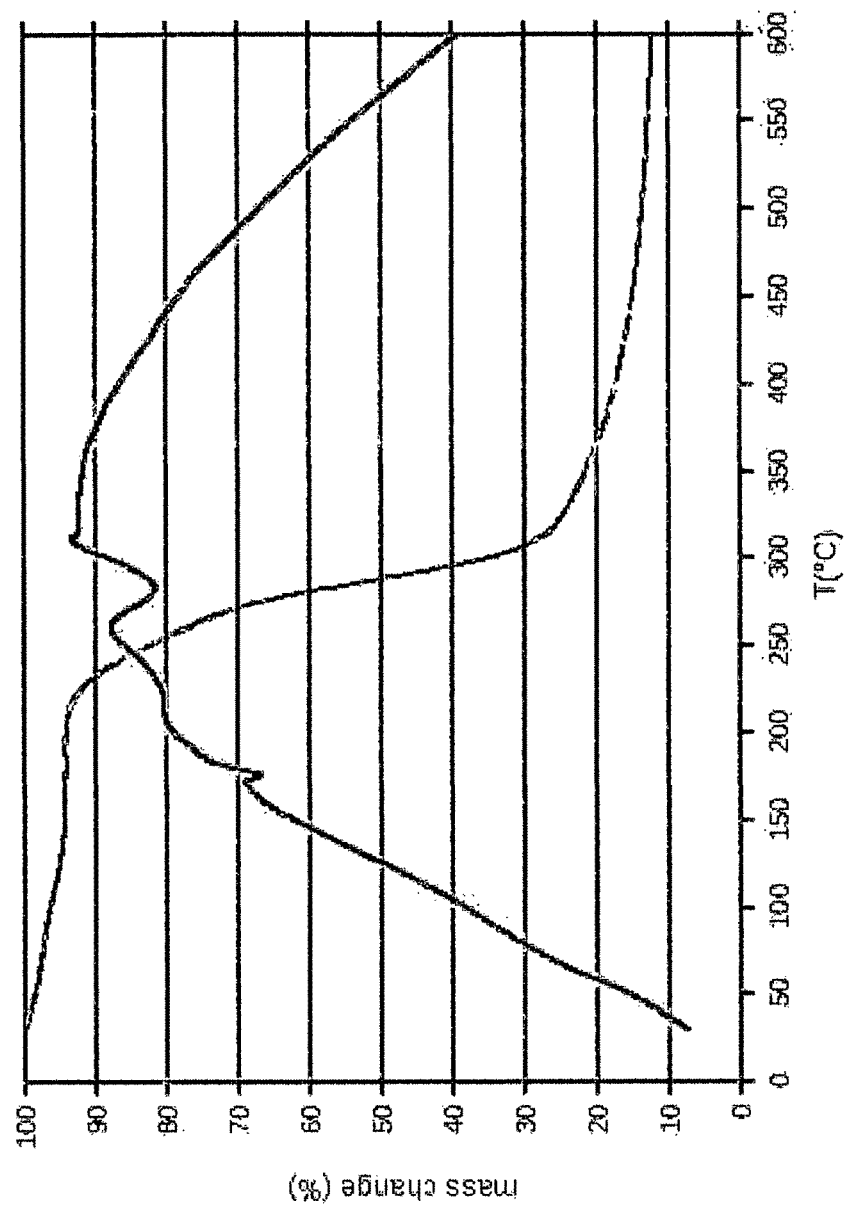
FIG. 6 Shows the thermogravimetric and differential thermal analysis of Polymorph A of Example 2

=TGA shows a loss of water of 5.45%, consistent with a type hydrated 1.5 times, See FIG. 6

Example 3

1371.6 measured g of 2'FL were concentrated to 58° Brix and heated to 55° C. 5.5 liters of absolute ethanol, heated to 56° C., were added over the course of 1 hour. The solution, already opalescent, was seeded and left hot, always under agitation, for several minutes, and then 1 liter of absolute ethanol heated to 50° C. was added. The suspension was left at 57° C. for 1 hour and 30 minutes, and then a cooling ramp was started that brought the temperature to 26° C. in 3 hours. The mixture was left overnight under agitation at room temperature, then filtered and washed with 1 volume of ethanol/water mixture=9/1. The solid was dried under vacuum (80 mbar) at 50° C. for 21 hours.

1412 grams were obtained with a titre of 92.6%.

KF=4.37%

$^1$HNMR (D$_2$O) at dissolution (300 MHz, nt=12): α anomer/β anomer=12/88

LOD=1.13% (Method 1)

Example 4

210 measured g of 2'-O-fucosyllactose were concentrated under vacuum and hot, at 70° Brix. The syrup was heated to 60° C. and, under agitation, 250 mL of 96% ethanol was added. The suspension was seeded, again with Polymorph A, and after 10 minutes under agitation and hot, a further 50 mL of 96% ethanol were added. The mixture was kept under agitation for 2 hours and 30 minutes at 60° C., and was then allowed to return slowly and spontaneously to r.t. After a few days (5) under agitation at room temperature, it was cooled to 10° C. and maintained at this temperature for 1 hour. The cooled solid was filtered, washed with 1 volume of ethanol/water=9/1 and 0.5 volumes of 96% ethanol, both cold. 206.8 grams of solid were obtained after drying at 55° C. under vacuum (80 mbar).

KF=4.54%

KF after 6 months=6.00%

LOD=2.17% after 6 months (Method 2)

PF=174-176

¹HNMR (DMSO) at dissolution (300 MHz; nt=1): α anomer/β anomer=14/86 Powder spectrum after 6 months: See FIG. 7

HPLC=purity 98.4%

Example 5

8 measured Kg of the 2'-O-Fucosyllactose were concentrated to 71 Brix. Over the course of 40 minutes, maintaining the temperature between 50-58° C., 17 liters of 96% ethanol were added. The solution was seeded and allowed to cool to room temperature over the course of 18-20 hours. The mixture was cooled to 15° C. in 4 hours and the solid was filtered, washed with 1 volume of ethanol/water mixture=9/1 and dried in a vacuum (80 mbar) at 60° C. 7.4 kg of dry solid were obtained.

KF=4.4
LOD=1.1% (Method 1)
PF=175-181° C.
¹HNMR ($D_2O$) at dissolution (300 MHz, nt=4): α anomer/β anomer=11/89
¹HNMR $D_2O$) at equilibrium after one night at room temperature (300 MHz; nt=1): α anomer/ρ anomer=39/61

Example 6

Figure 8:
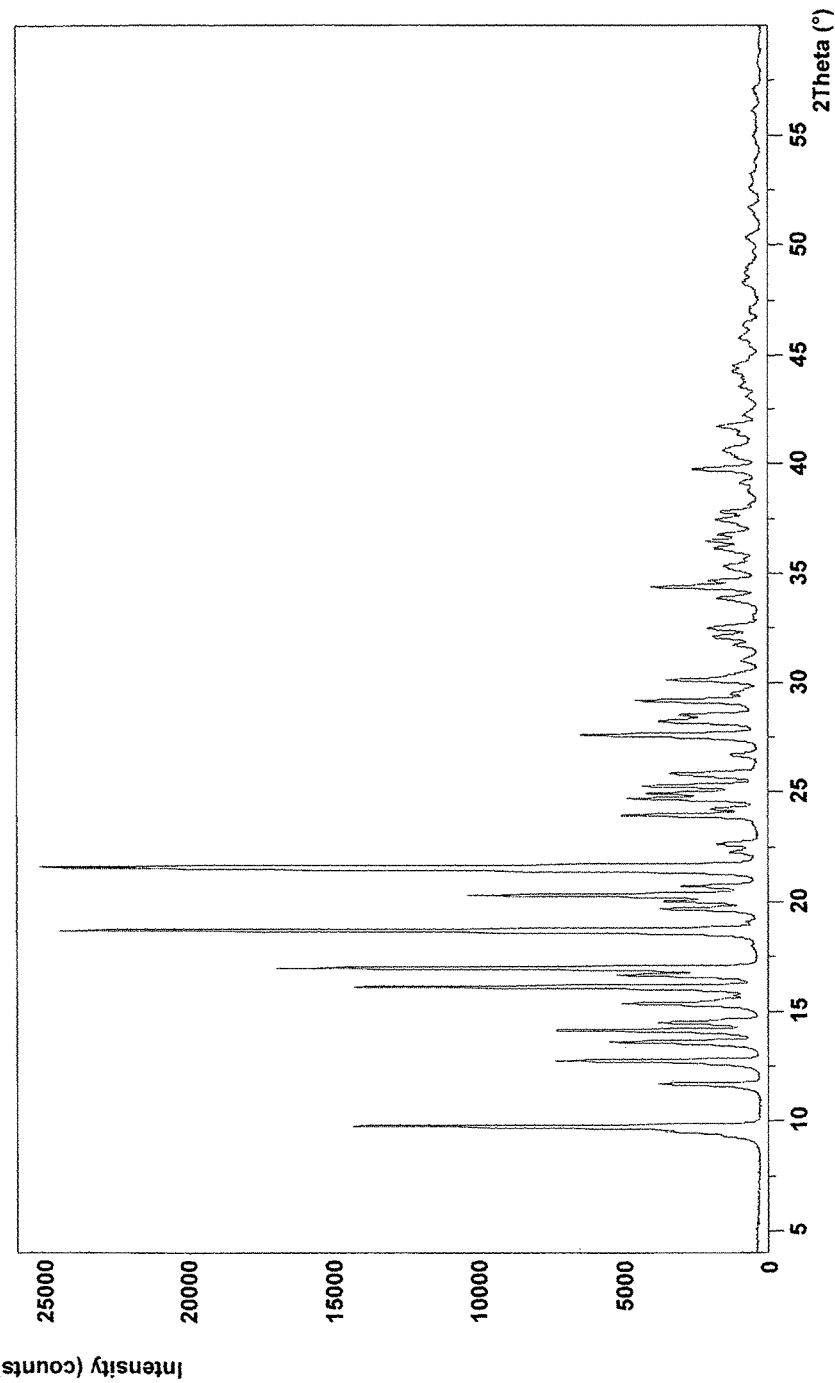
FIG. 8 Shows the X-ray powder diffraction spectrum of the 2'-O-Fucosyllactose Polymorph A of Example 6
Figure 9:
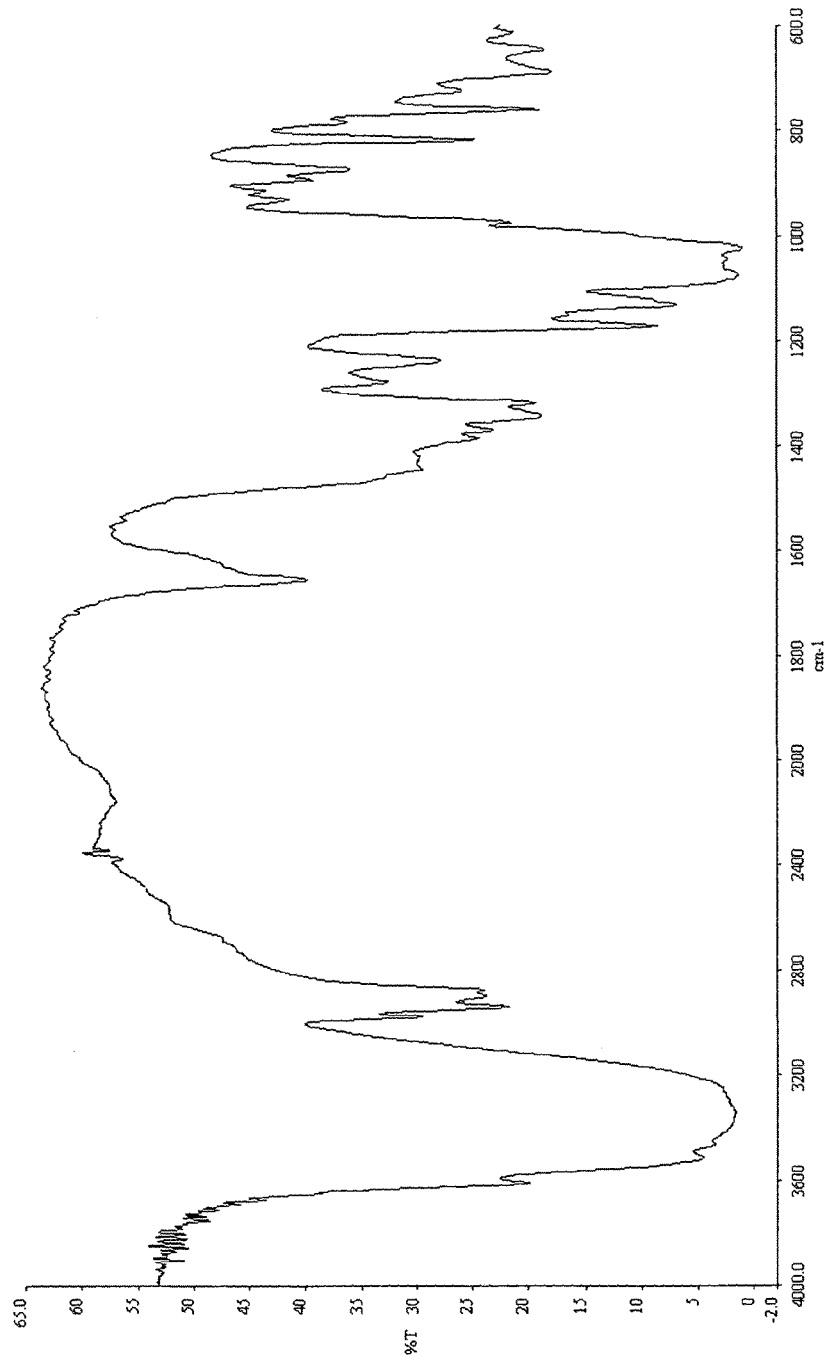
FIG. 9 Shows the IR spectrum of the 2'-O-Fucosyllactose Polymorph A of Example 6
Figure 10:
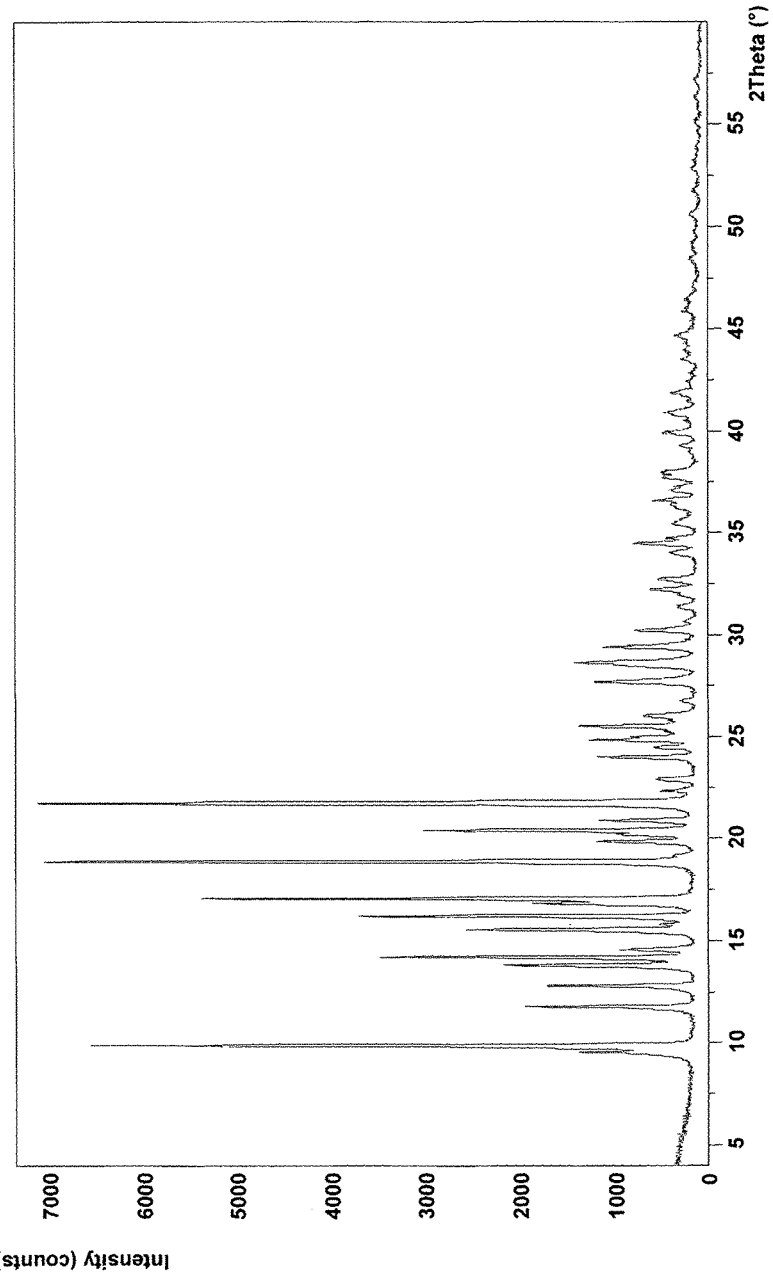
FIG. 10 Shows the X-ray powder diffraction spectrum of the 2'-O-Fucosyllactose Polymorph A of Example 7

10 g of the 2'-O-Fucosyllactose were dissolved hot at 60° Brix. The solution, weighing 16.5 g, was maintained at 55° C. during the addition of 32.5 mL of Propanol heated to 60° C. Mid-addition opalescence was noted. At full addition the suspension was left for 1 hour at 55-60° C. and then, again under strong agitation, it was allowed to return spontaneously to room temperature. After about 12 hours at room temperature the suspension was cooled to 15° C. over 1 hour. The solid was filtered, washed with 1 volume of propanol/water=9/1 and dried in a vacuum (80 mbar) at 55° C. for the night and stored in a desiccator with silica gel for 18 hours. 8.95 g of dry solid were obtained that presents:

KF=5.11%
LOD=1.30% (Method 2); 2.14% (Method 1)
PF=175-186
¹HNMR (DMSO) at dissolution (200 MHz, nt=24): α anomer/β anomer=8/92
Powder XRPD spectrum=Shows the phase of Polymorph A (2'FL.1.5$H_2O$) See FIG. 8
IR=3340, 1.62; 2977, 29; 2940, 22; 1656, 40; 1343, 19; 1237, 27; 1171, 8; 1132, 7; 1072, 1; 1023, 1; 875, 36; 819, 25; 762, 19; 722, 38; 688, 18; 646, 19. See FIG. 9
HPLC=purity 99.5%

Example 7

50 g 2'FL were brought to a syrup of 72.5° Brix. At 30° C. it was diluted with 70 mL of methanol heated to 35° C. and primed. The mixture was allowed to return to room temperature under agitation. The suspension was heated again to 40° C. and 70 mL of methanol heated to 45° C. were added. The suspension was allowed to return to room temperature and kept under agitation for a few days.

The solid was filtered, washed with 50 mL of cold methanol and dried at ambient pressure and temperature. 42 g of dry product were obtained KF=5.16%
LOD=2.22% (Method 1); 1.30 (Method 2)
PF=176-186
¹HNMR (DMSO) at dissolution (200 MHz, nt=12): α anomer/β anomer=8/92

Figure 11:
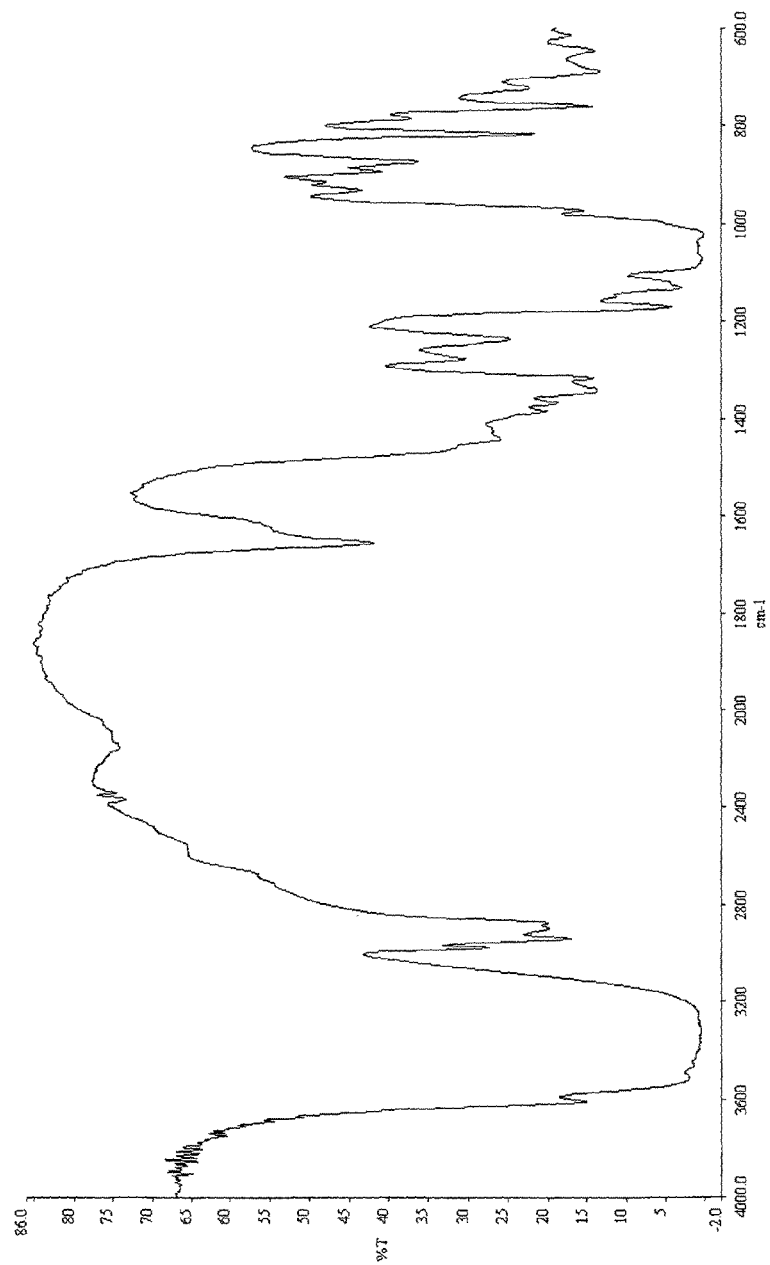
FIG. 11 Shows the IR spectrum of the 2'-O-Fucosyllactose Polymorph A of Example 7

¹HNMR (DMSO) at equilibrium after one night at room temperature (200 MHz, nt=12): α anomer/β anomer=24/76
¹HNMR (D2O) at dissolution (200 MHz, nt=20): α anomer/β anomer=12/88;
Powder spectrum=Shows the phase of the Polymorph (2'FL.3/2$H_2O$). See Figure
IR=3334, 1; 2976, 27; 2939, 17; 1657, 42; 1386, 20; 1344, 14; 1237, 25; 1172, 4; 1132, 3; 1072, 1; 1025, 1; 875, 36; 819, 21; 762, 14; 724, 22; 689, 13; 646, 14. See FIG. 11

Example 8

10 g of 2'FL of Polymorph A were dissolved in water (5.6 g), whilst hot, 640 Brix. The solution was maintained at 60° C. during the addition of acetone heated to 50° C. The addition was completed in thirty minutes. After a further 30 minutes under agitation whilst hot, the mixture was allowed to return spontaneously to room temperature. After 10 hours under agitation at room temperature the suspension was cooled to 10° C. in 1 hour, filtered and washed with 10 mL of cold acetone. The solid was dried in a stove under a vacuum (80 mbar) at 50° C. and stored in a desiccator for 20 hours. 9.29 grams of dry product were obtained.

Figure 12:
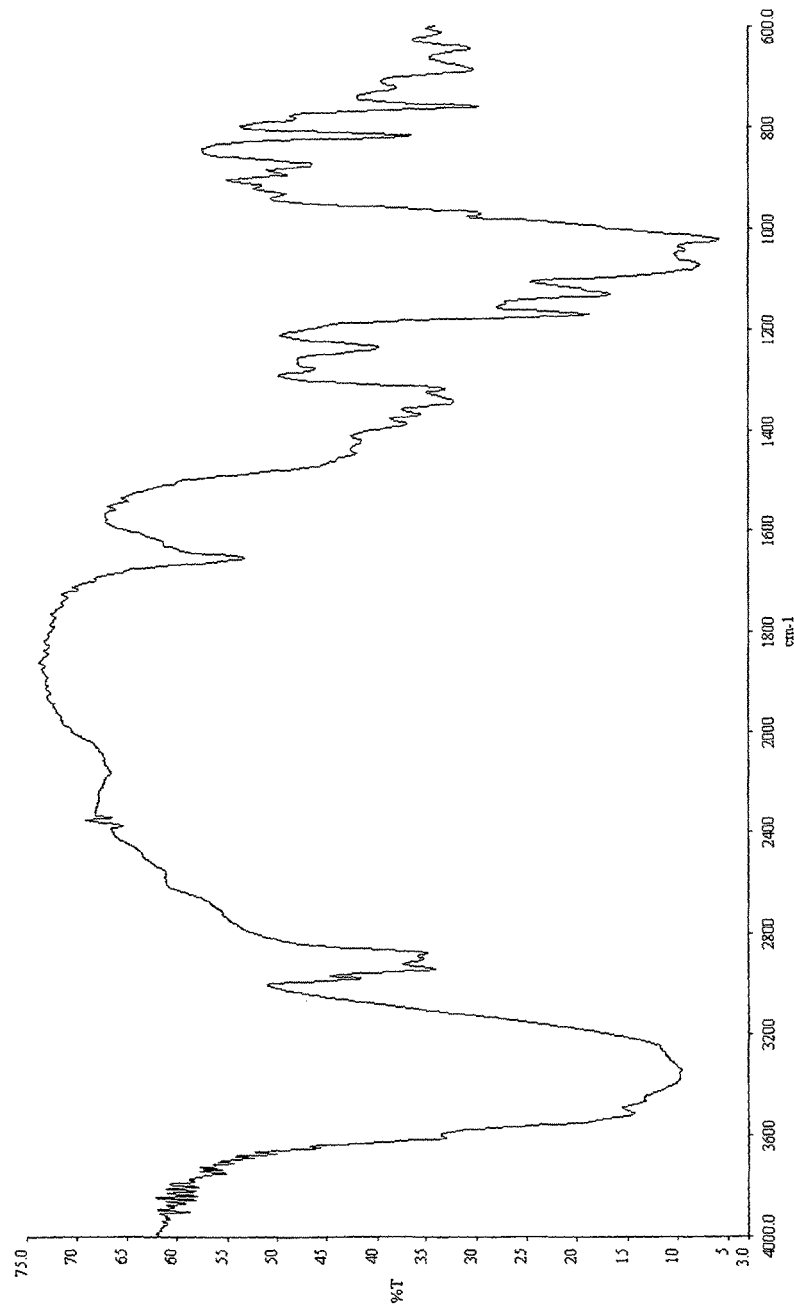
FIG. 12 Shows the IR spectrum of the 2'-O-Fucosyllactose Polymorph A of Example 8
Figure 13:
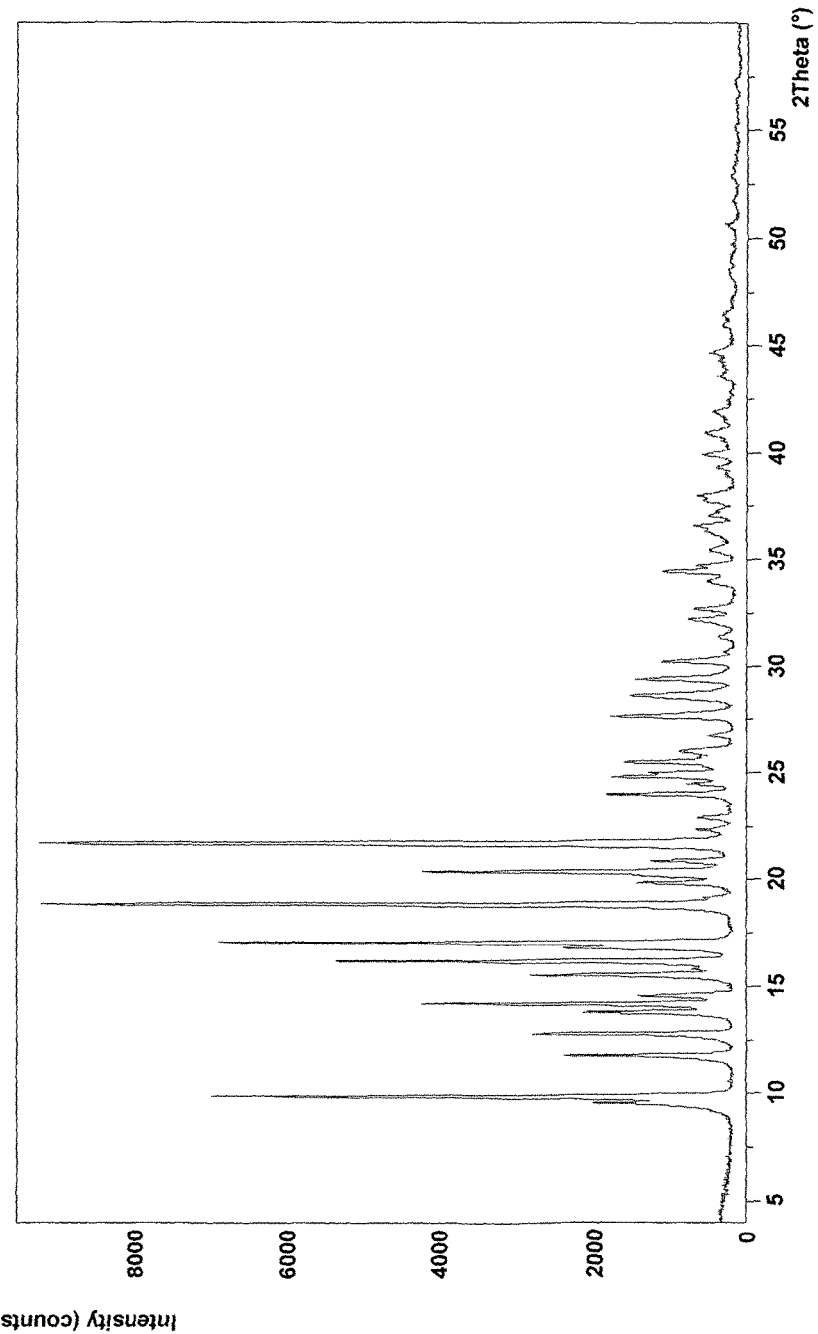
FIG. 13 Shows the X-ray powder diffraction spectrum of the 2'-O-Fucosyllactose Polymorph A of Example 8

KF=4.7%
LOD=1.39 (Method 2), 2.21 (Method 1)
¹HNMR ($D_2O$) at dissolution (300 MHz, nt=20) α anomer/β anomer=13/87
PF=175-179
IR=3340, 10; 2978, 42; 2940, 34; 2875, 35; 1655, 53; 1343, 32; 1237, 40; 1172, 19; 1132, 17; 1072, 8; 1023, 6; 875, 46; 818, 36; 761, 30; 687, 30; 645, 30. See FIG. 12
Powder spectrum: Shows the phase of Polymorph A (2'FL.3/2$H_2O$). FIG. 13

Example 9

Figure 14:
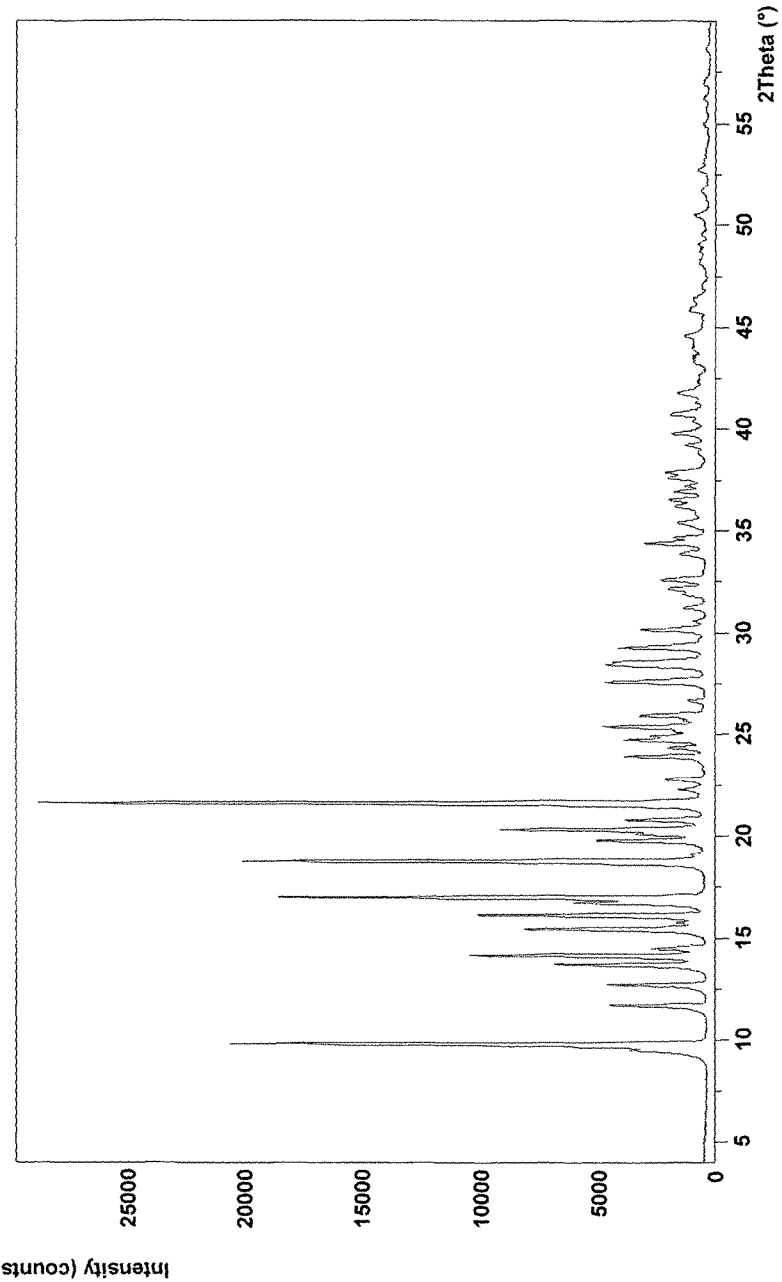
FIG. 14 Shows the X-ray powder diffraction spectrum of the 2'-O-Fucosyllactose Polymorph A of Example 9

5 g of 2'FL, dried from syrup, were dissolved in water until solubilisation. Totally 5.3 g of water were used. Under agitation, at 60° C., 20 mL of glacial acetic acid were added. At full addition slight opalescence was noticed. The suspension was maintained a further 1 hour at 60° C. and then the heating was stopped and it was left under agitation overnight. After about 10 hours at room temperature, the solid was filtered, washed with 1 volume of 80% acetic acid and dried under vacuum (80 mbar) at 55° C. for 16 hours and in a desiccator for 6 hours. 2.87 g of dry solid were obtained, presenting:

KF=4.37%
LOD=0.74% (Method 2)
PF=175-183° C.
¹HNMR ($D_2O$) at dissolution (200 MHz, nt=120): α anomer/β anomer=12/88
Powder spectrum: see FIG. 14

Example 10

10 g of 2'FL, dried from syrup, were dissolved in water until solubilisation. The solution was brought to 64° Brix and 60 mL of acetonitrile at 50° C. were added dropwise, whilst hot (60° C.) and under energetic agitation. Opalescence was already noted mid-addition. The suspension was maintained 30 minutes under agitation at 60° C. and then the heating was turned off and it was allowed to return, slowly and spontaneously to room temperature. After 10 hours at room temperature, the mixture was slowly cooled to 10° C.

Figure 15:
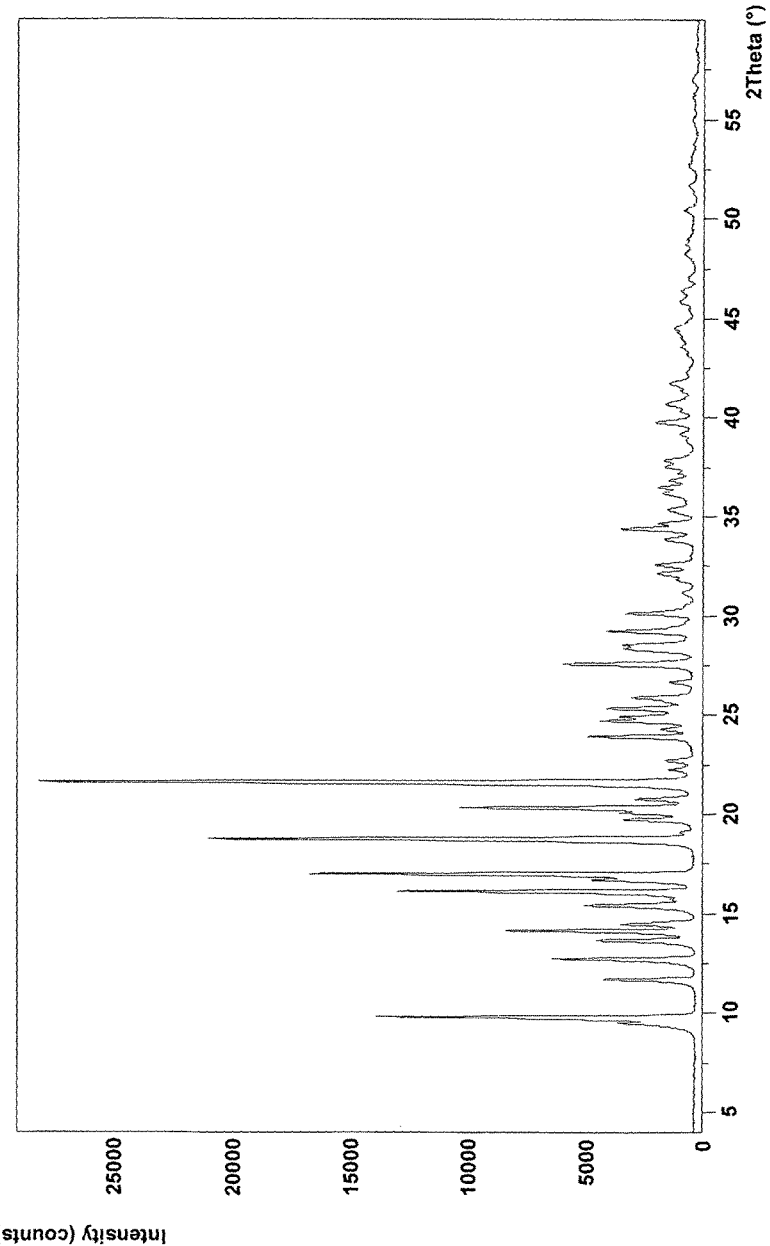
FIG. 15 Shows the X-ray powder diffraction spectrum of the 2'-O-Fucosyllactose Polymorph A of Example 10

The solid was filtered, washed with 1 volume of acetonitrile cooled to 10° C., and dried under vacuum (80 mbar) at 55° C. for 4 hours (9.3 g).
KF=4.67%
LOD=2.51 (Method 1); 0.93 (Method 2)
PF=176-179
$^1$HNMR (D$_2$O) at dissolution (300 MHz, nt=20): α anomer/β anomer=12/88
$^1$HNMR (D$_2$O) at equilibrium after one night at room temperature (200 MHz, nt=16): α anomer/β anomer=40/60
Powder spectrum: see FIG. 15

Example 11

Figure 16:
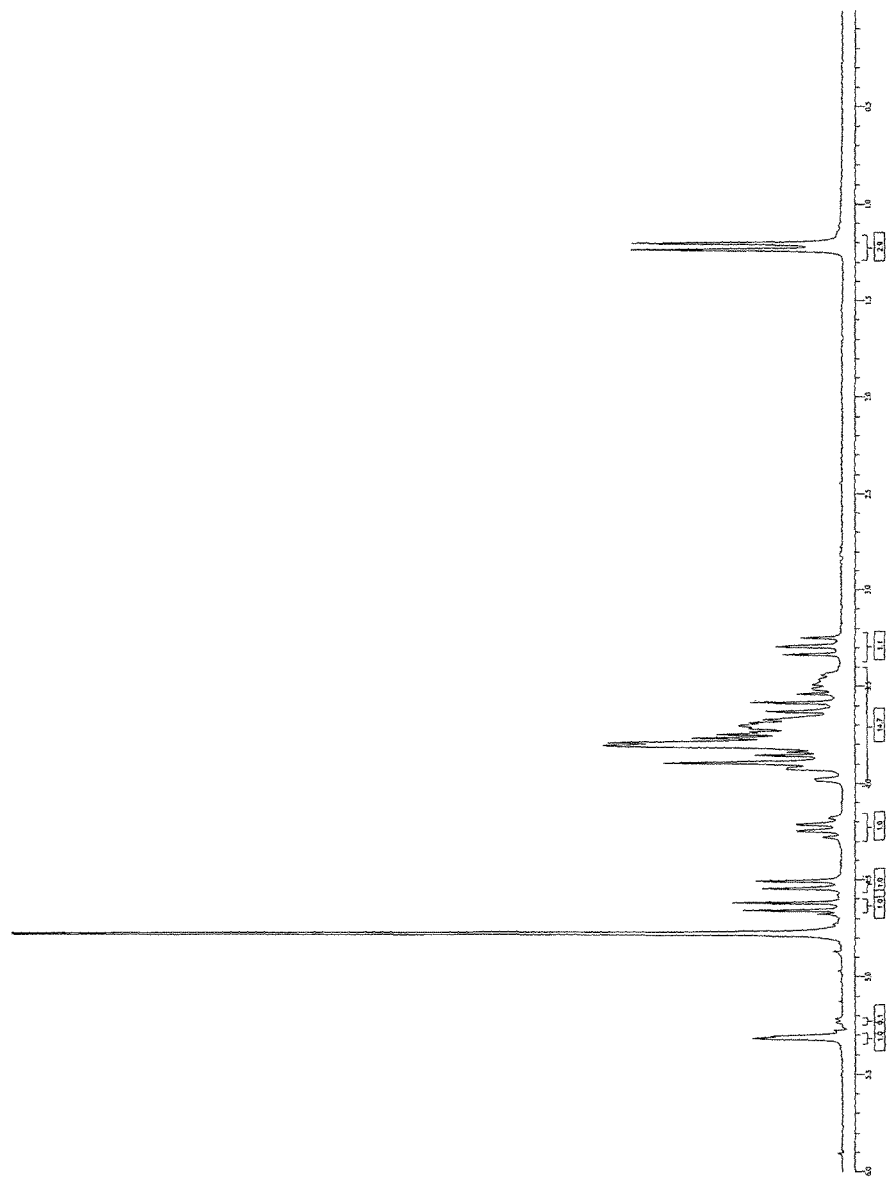
FIG. 16 Shows the $^1$HNMR spectrum of the 2'-O-Fucosyllactose Polymorph A of Example 11

20 g of 2'FL, dried from syrup, were dissolved at 64° Brix, heated to 55° C. and 75 mL of a mixture of methanol/ethanol=3/2 heated to 50° C. was added. At the end of the dropwise addition the solution was brought to 62° C.; it already had a suspension. After 1 hour at 62° C. the temperature was lowered to 56° C., maintained for 3 hours and then allowed to return spontaneously to room temperature. After 12-15 hours under agitation at room temperature, the solid was cooled to 3° C., filtered, washed with 1 volume of a mixture of methanol/ethanol/water=3/4/1 and dried in a vacuum (80 mbar) at 55° C. for 2 hours.
KF=4.46%
LOD=1.89%
$^1$HNMR (D$_2$O) at dissolution (300 MHz, nt=20): α anomer/β anomer=6/94. See FIG. 16
$^1$HNMR (D$_2$O) at equilibrium after one night at room temperature. (300 MHz, nt=20): α anomer/β anomer=42/58

Example 12

20 g of 2'FL Ex. 3 were dissolved in water and concentrated to 56° Brix. The solution was heated to 60° C. and under agitation 75 mL of absolute ethanol heated to 57° C. was added. The mixture was kept 1 hour at 66-64° C., 14 hours at 60° C., and then cooled to 5-8° C. in 3-4 hours. The solid was filtered, washed with a water/ethanol mixture and dried both at ambient temperature and pressure (15 hours) and in a vacuum (80 mbar) at 55° C. for 4 hours to obtain 16.33 g of solid.
KF=4.61%
LOD=1.24% (Method 1)
$^1$HNMR (D$_2$O) at dissolution (200 MHz, nt=28): a anomer/1 anomer=9/91

Example 13

Figure 17:
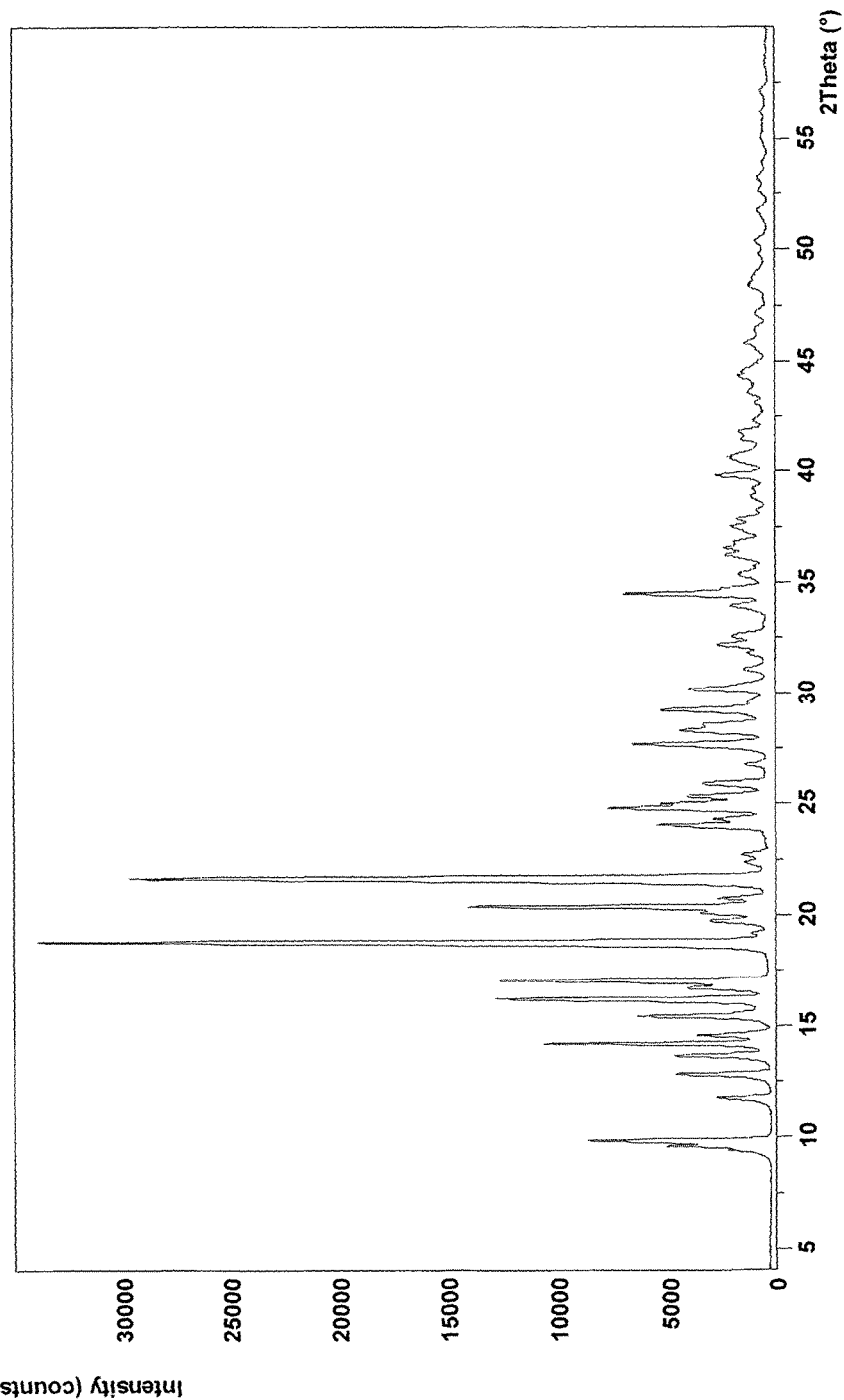
FIG. 17 Shows the X-ray powder diffraction spectrum of the 2'-O-Fucosyllactose Polymorph A of Example 13

6.59 g of 2'FL Polymorph B were placed on a petri dish placed in a desiccator with anhydrous silica gel for 46 hours. The solid was removed from the dryer and analysed.
KF=4.37%
LOD=2.41% (Method 1)
Powder spectrum=Shows the phase of Polymorph A (2'FL.3/2H$_2$O). See FIG. 17

Example 14

Figure 18:
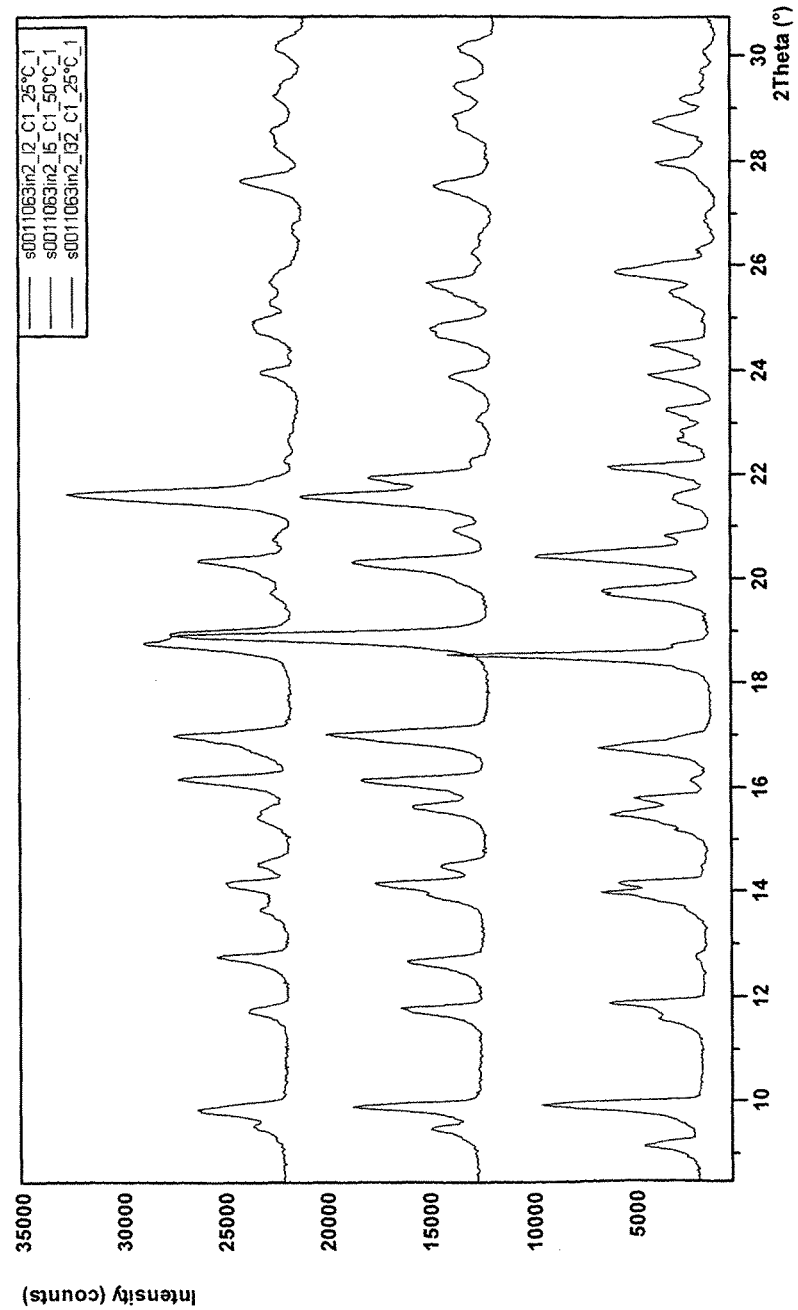
FIG. 18 Shows the X-ray powder diffraction spectrum at different temperatures of the 2'-O-Fucosyllactose Polymorph A and B of Example 14

50 mg of Polymorph B were subjected to powder thermodiffractometry. The powder was heated, with a heating ramp of 5° C./min, up to 150° C. and then gradually cooled, with the same mode as for heating, at 25° C. Once at room temperature Polymorph A is obtained.
Powder spectrum=from Polymorph B by heating and subsequent cooling one obtains Polymorph A passing through a new crystalline phase. The spectrum of Polymorph A, immediately recorded after cooling still contains a small percentage of the anhydrous polymorph. See FIG. 18
Polymorph B Example 15

Figure 19:
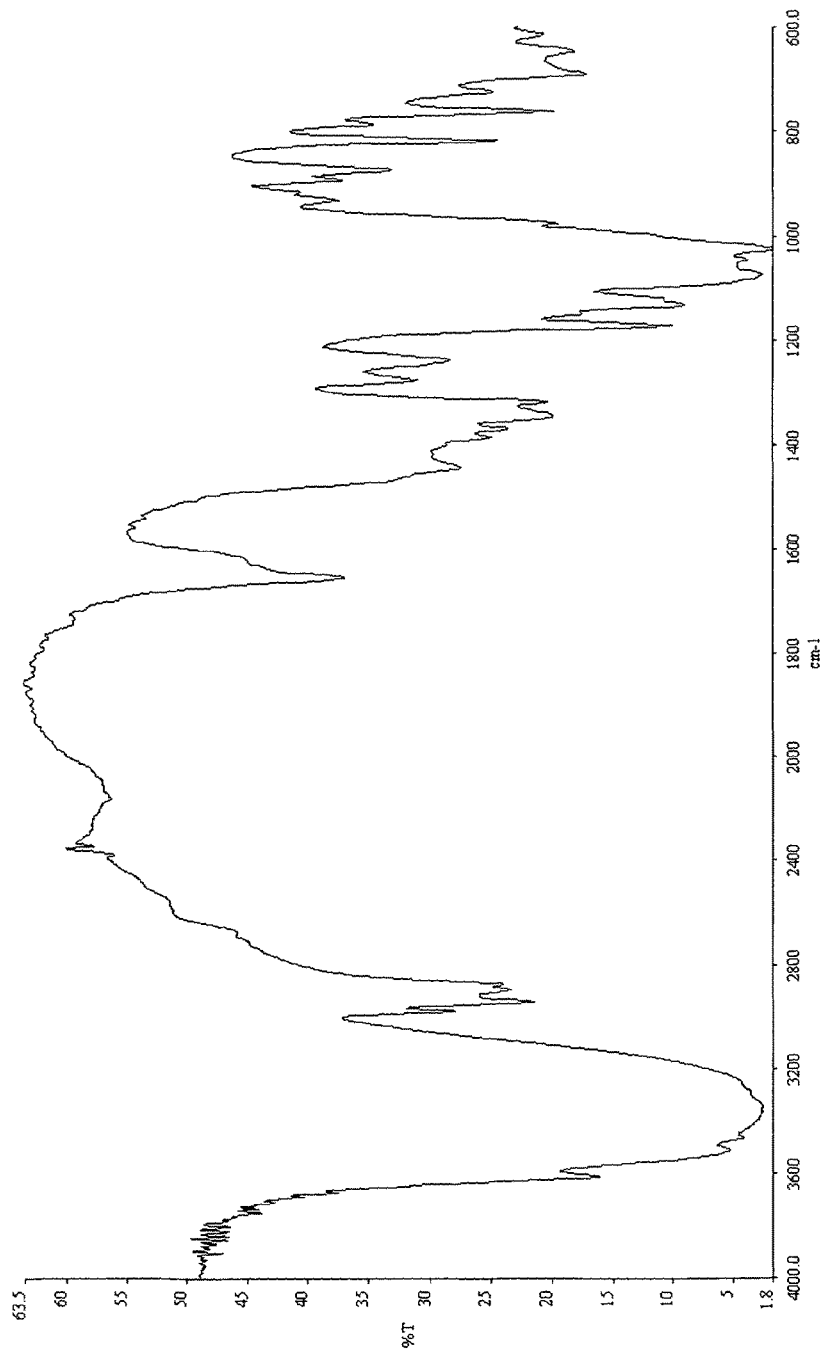
FIG. 19 Shows the IR spectrum of the 2'-O-Fucosyllactose Polymorph B of Example 15
Figure 20:
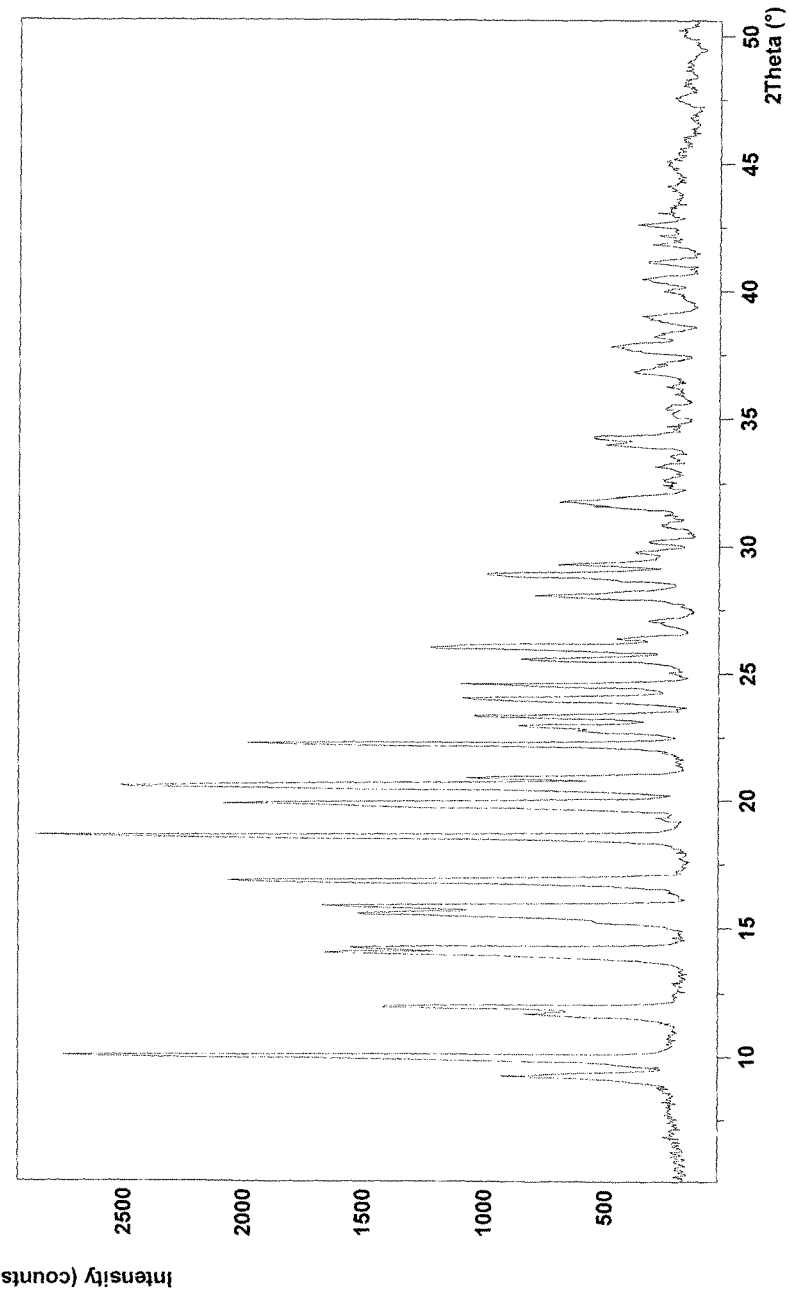
FIG. 20 Shows the X-ray powder diffraction spectrum of the 2'-O-Fucosyllactose Polymorph B of Example 15

22.9 kg of 2'FL were concentrated to 79° Brix. At 38° C. the syrup self-seeded. 600+400 mL of water were added to the suspension and it was left under agitation at 38-48° C. for 1 hour, then left to reach room temperature during the night. The suspension was kept under agitation at 23-28° C. for one day, then cooled to 15±2° C. in 6 hours and filtered. The solid was washed with 0.05V of cold water and dried in a stove under a vacuum, first at 30° C., then at 35° C. for 15 hours. 18.4 kg of dry solid were obtained.
KF=8.31%
LOD=6.6% (Method 1)
PF=176-181
$^1$HNMR (DMSO) at dissolution (300 MHz; nt=20): α anomer/β anomer=4/96
$^1$HNMR (DMSO) at equilibrium after one night at room temperature (300 MHz, nt=12): α anomer/β anomer=18/82
$^1$HNMR (DMSO) at equilibrium after 5 days (300 MHz, nt=12): α anomer/β anomer=48/52
IR=3342, 3; 2975, 28; 2939, 21; 2894, 23; 1657, 37; 1445, 27; 1370, 24; 1347, 20; 1318, 20; 1278, 31; 1238, 28; 1172, 10; 1132, 9; 1072, 3; 1023, 2; 932, 38; 895, 37; 874, 33; 819, 24; 762, 20; 690, 17; 647, 18. (See FIG. 19)
Powder XRPD spectrum=Shows the phase of Polymorph B (2'FL.5/2H$_2$O). See FIG. 20

Example 16

24.8 g of 2'FL were concentrated at 77° Brix, and seeded with 200 mg of Polymorph B at 37° C. The suspension was left at 40±4° C. for 4 hours and then, always under agitation, it was allowed to return spontaneously to room temperature. The suspension was maintained about 24 hours at 23° C. then cooled and filtered at 18° C. The solid was washed with water at 4° C. (400 mg×3) and dried under vacuum (80 mbar) whilst hot (35-40° C.) for 11 hours plus one night in static vacuum without heating. 17.7 g of solid were obtained.
KF=7.99%
LOD=5.18% (Method 1) 18.4% (Method 2)
PF=178-184
$^1$HNMR (D$_2$O) at dissolution (300 MHz, nt=4): α anomer/β anomer=8/92

Example 17

Figure 21:
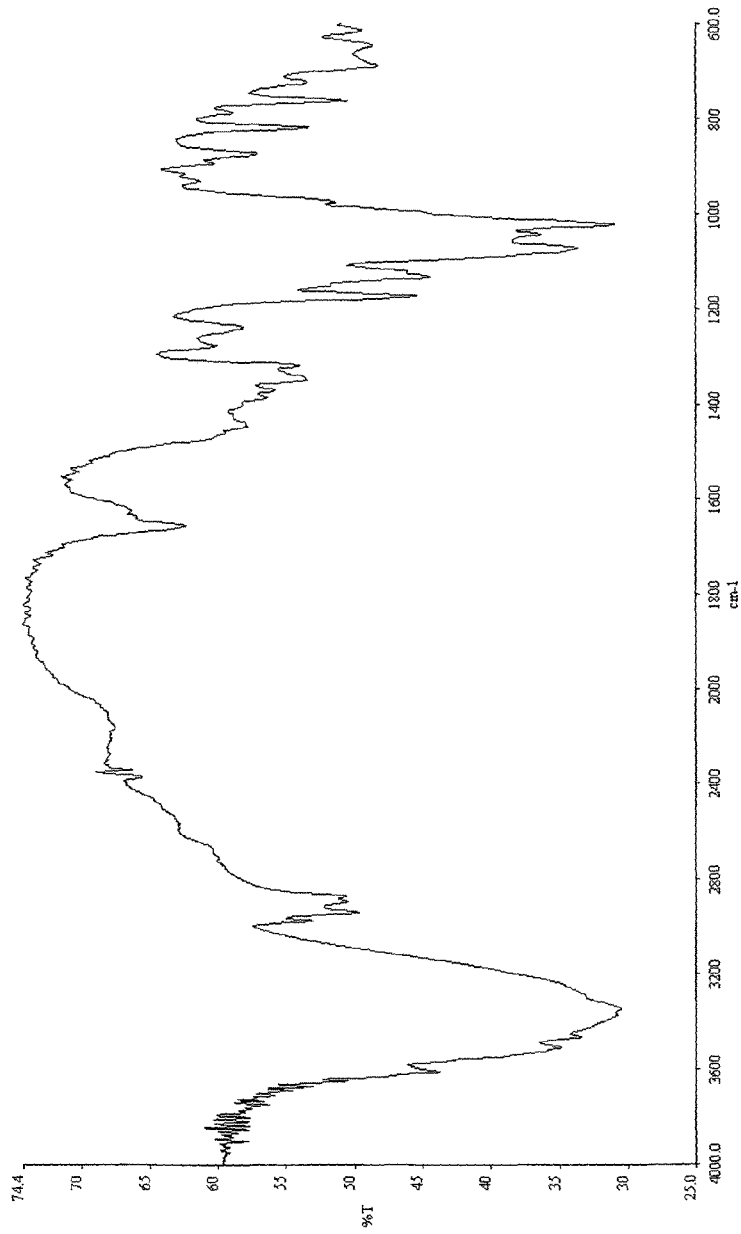
FIG. 21 Shows the IR spectrum of the 2'-O-Fucosyllactose Polymorph B of Example 17

67 Kg of Fucosyllactose Polymorph A were dissolved in water and concentrated to 74° Brix. The solution was brought to 40° C., seeded with Polymorph B and left 2 hours under agitation whilst hot. The heating was turned off and the suspension was allowed to return slowly to 21° C. The solid was kept under agitation at 20-22° C. for 24 hours and then cooled to 15° C. The suspension was maintained for 6 hours at 15° C. and cooled to 10° C. After 3 hours at 10° C. the solid was centrifuged and washed with 0.10 volumes of water at 5° C. The solid was dried in a vacuum (80 mbar) at 35° C. for 10 hours and in static vacuum without heating for 10 hours.
KF=8.88
LOD=6.4 (Method 1); 5.36 (Method 2)
$^1$HNMR (DMSO) at dissolution (200 MHz; nt=4): α anomer/β anomer=6/94 IR=3344, 31; 2939, 50; 1656, 62;

1348, 53; 1239, 58; 1173, 45; 1133, 44; 1072, 34; 1023, 31; 874, 57; 819, 53; 762, 51; 688, 48. (See FIG. 21)

Figure 22:
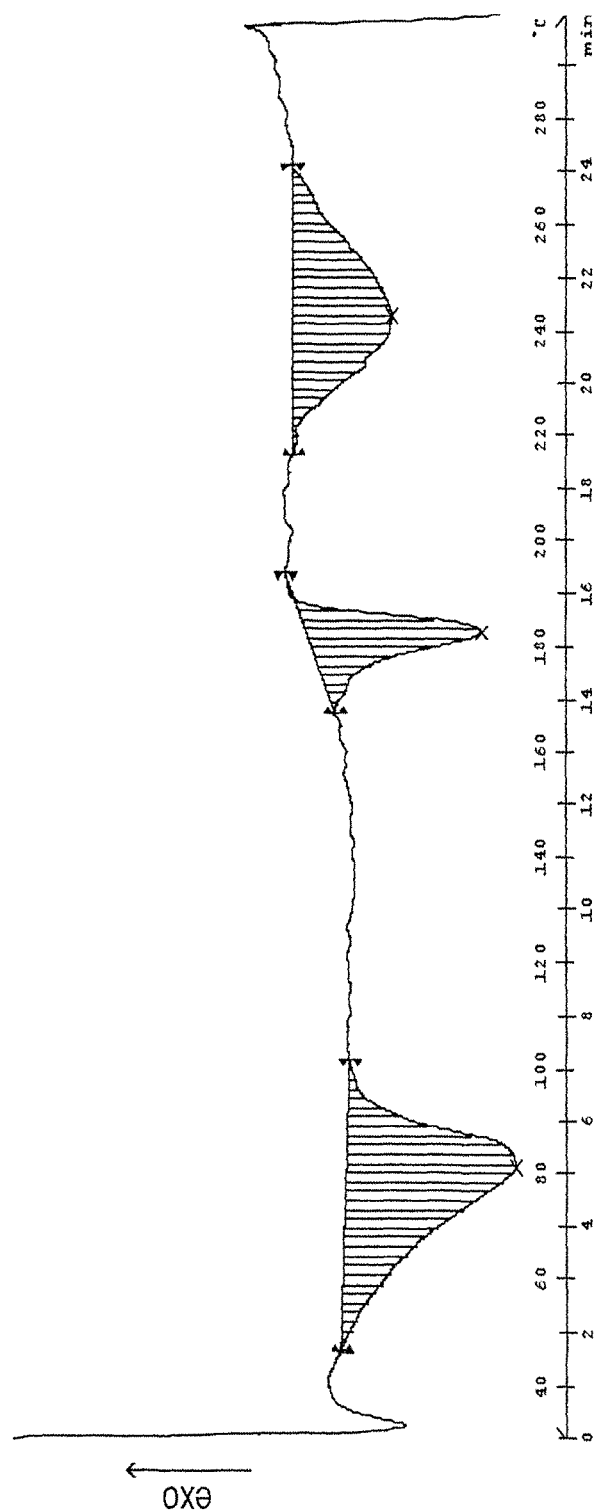
FIG. 22 Shows the differential scanning calorimetry analysis curve of the 2'-O-Fucosyllactose Polymorph B of Example 17

DSC: Initial broadened endothermic effect (55-100° C.) attributable to phenomena of dehydration, followed by an intense endothermic peak ($T_{start}$=173.92° C.; $T_{peak}$=181.73° C.) attributable to the melting of the sample. At higher temperatures it is followed by an intense endothermic band with a peak at 241.8° C., due to decomposition phenomena. (See FIG. 22)

Figure 23:
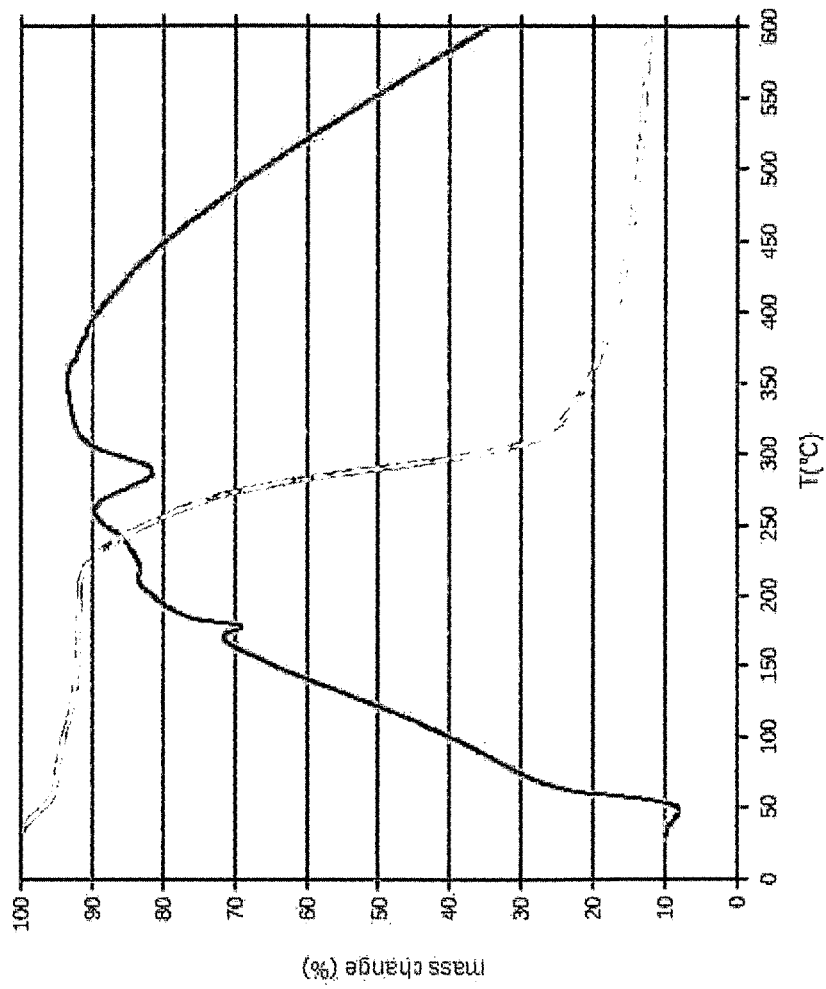
FIG. 23 Shows the thermogravimetric and differential thermal analysis of Polymorph B of Example 17

TGA=shows a loss of water of 7.90% compatible with the type hydrated 2.5 times (2'FL.5/2H$_2$O). See FIG. 23

Powder XRPD spectrum: Shows the phase of Polymorph B (2'FL.5/2H$_2$O) and Polymorph A (less than 5%).

Figure 24:
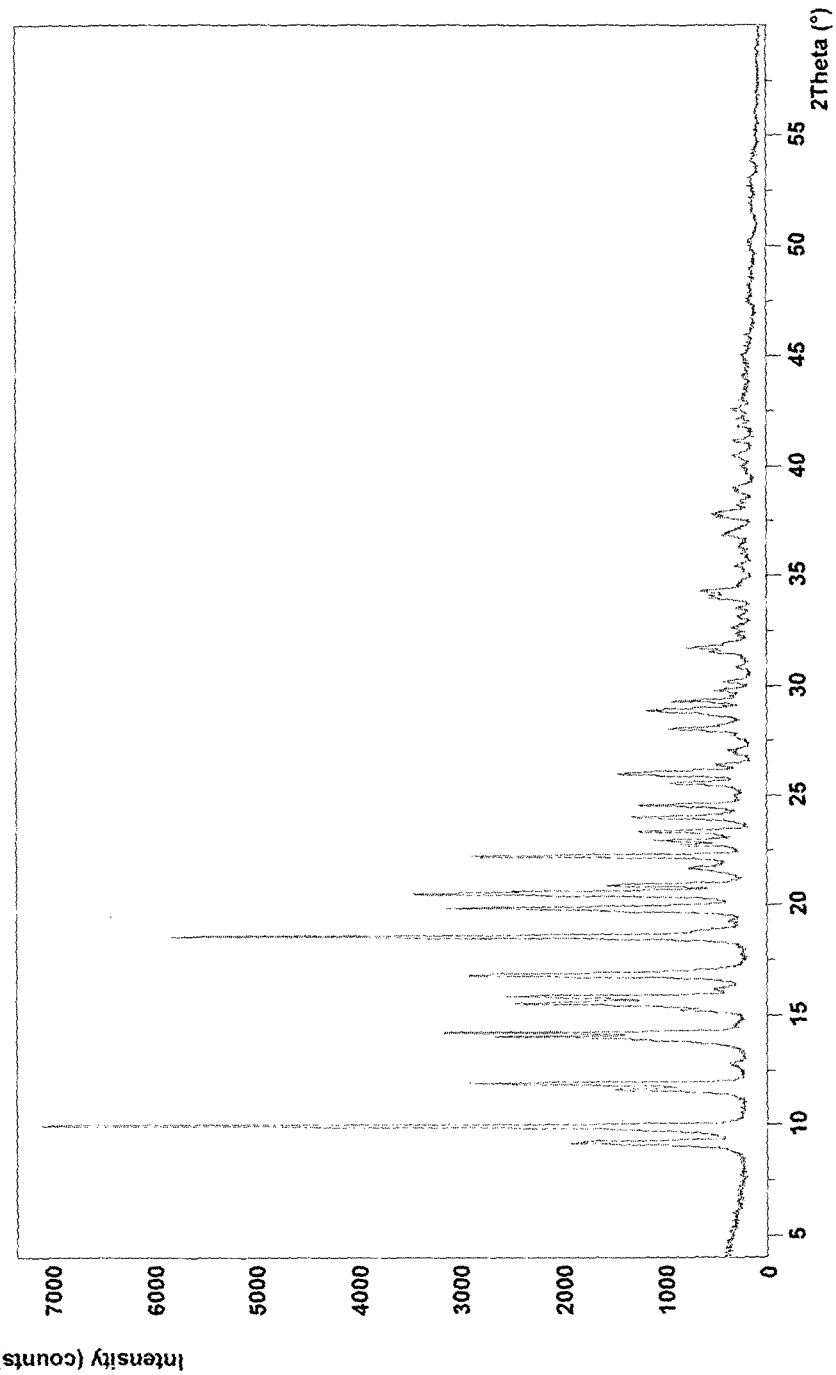
FIG. 24 Shows the X-ray powder diffraction spectrum of the 2'-O-Fucosyllactose Polymorph B of Example 17

The spatial group in which it crystallises is P2$_1$2$_1$2$_1$. The cell is orthorhombic with volume of 2349.4 Å$^3$.

a (Å)=14.905(7)
b (Å)=12.663(6)
c (Å)=12.447(5)
α(°)=90
β(°)=90
γ(°)=90
See FIG. 24

Example 18

Figure 25:
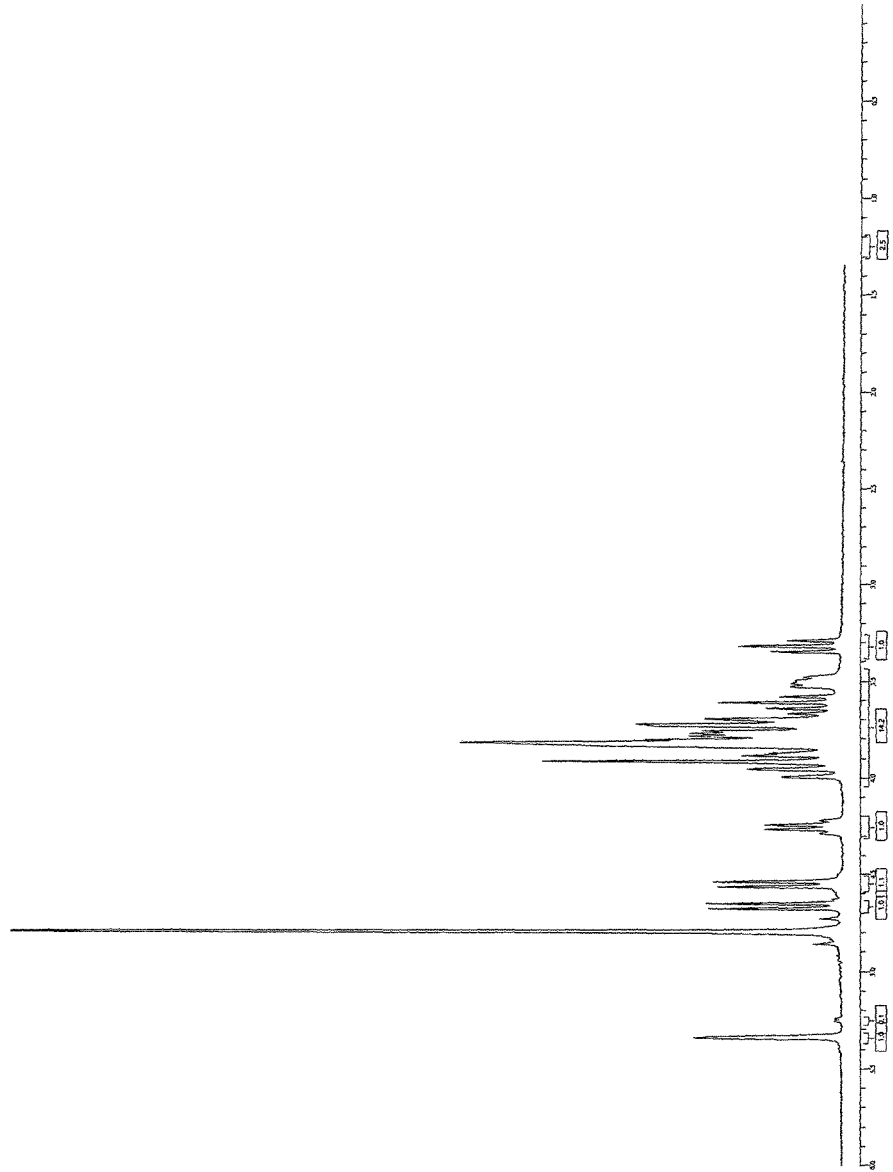
FIG. 25 Shows the $^1$HNMR spectrum of the 2'-O-Fucosyllactose Polymorph B of Example 18

88 g of 2'FL were concentrated to 70° Brix. The syrup heated to 40° C. crystallises spontaneously. After 1 hour under agitation at 40° C. it was cooled to 30° C., maintained for 2 hours, and then allowed to return spontaneously to room temperature. After 10 hours at room temperature the suspension was cooled in 3 hours at 5° C. After being kept cool for 2 and a half hours the solid was filtered, washed with 0.1 volumes of chilled water, and dried in a vacuum (80 mbar) at 35° C. for 6 hours to obtain 51 g of product KF=8.10%
LOD=6.14% (Method 1)
PF=179-181
$^1$HNMR (D$_2$O) at dissolution (300 MHz, nt=4): α anomer/β anomer=7/93. See FIG. 25
$^1$HNMR (D$_2$O) at equilibrium after one night at room temperature (300 MHz, nt=4): α anomer/β anomer=41/59
HPLC=purity 98.4%
Polymorph C Example 19

200 mL of a methanol/propanol mixture=2/1 were added over 20 minutes whilst warm (60° C.) to 10 grams of 2'-O-Fucosyllactose (Polymorph A). After 30 minutes whilst warm the heating was turned off in order to slowly return the mixture to room temperature overnight.

After 10-12 hours under agitation at room temperature the suspension was cooled to 10-15° C. The solid was filtered, washed with 1 volume of cold propanol/methanol mixture=1/2 and dried under vacuum (80 mbar) at 55° C. for two hours and 20 hours in a desiccator to obtain 7.2 g of product.

Figure 26:
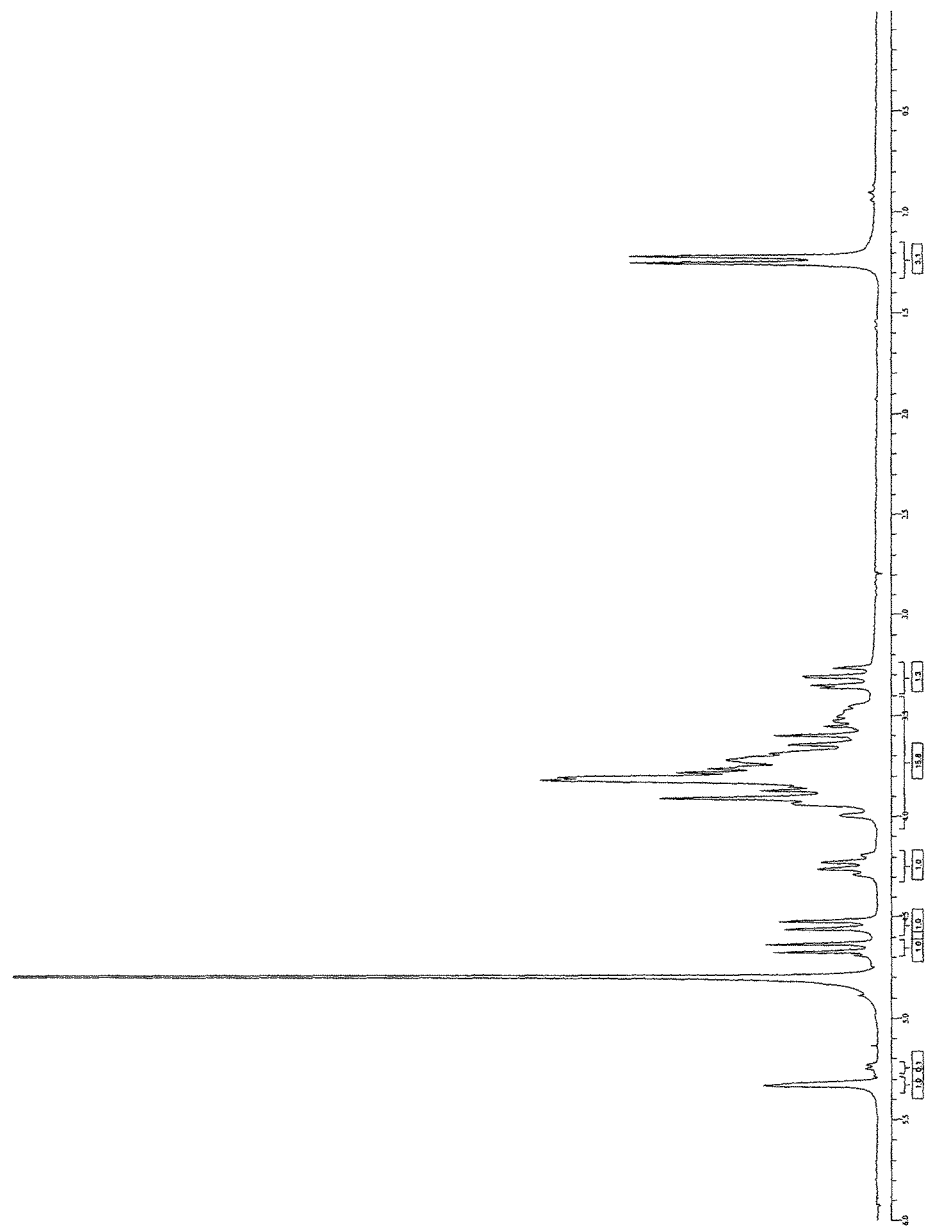
FIG. 26 Shows the $^1$HNMR spectrum of the 2'-O-Fucosyllactose Polymorph C of Example 19
Figure 27:
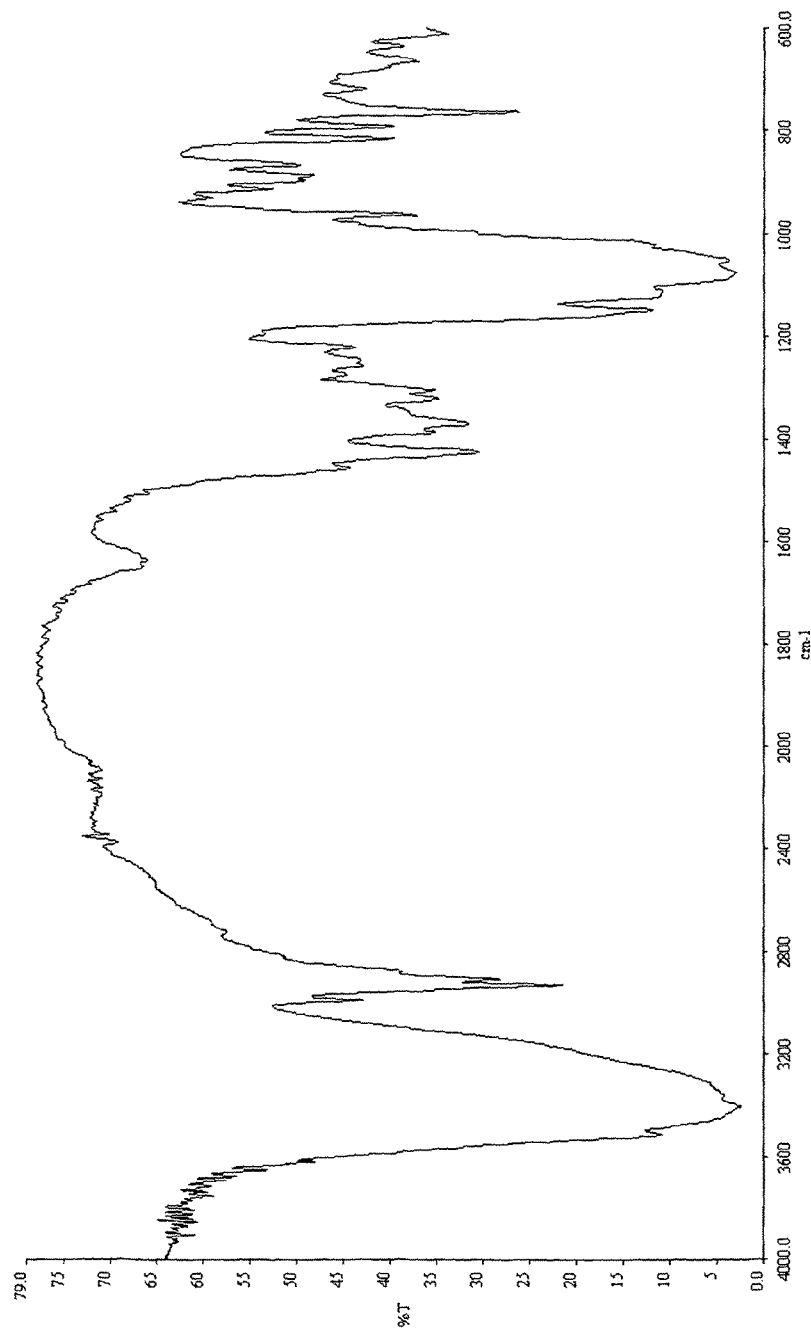
FIG. 27 Shows the IR spectrum of the 2'-O-Fucosyllactose Polymorph C of Example 19

KF=0.24%
KF after 2 months=0.34%
LOD=7.1% (Method 1)
PF=212-216
$^1$HNMR (D$_2$O) at dissolution (200 MHz, nt=64): α anomer/β anomer=9/91, See FIG. 26
$^1$HNMR (DMSO) at dissolution (300 MHz; nt=1): α anomer/β anomer=8/92 IR=3403, 2; 2990, 43; 2931, 21; 2908, 28; 1636, 66; 1425, 30; 1371, 32; 1306, 35; 1222, 44; 1149, 12; 1076, 3; 965, 37; 889, 48; 868, 50; 818, 40; 794, 39; 765, 26; 666, 37; 637, 39. See FIG. 27

Figure 28:
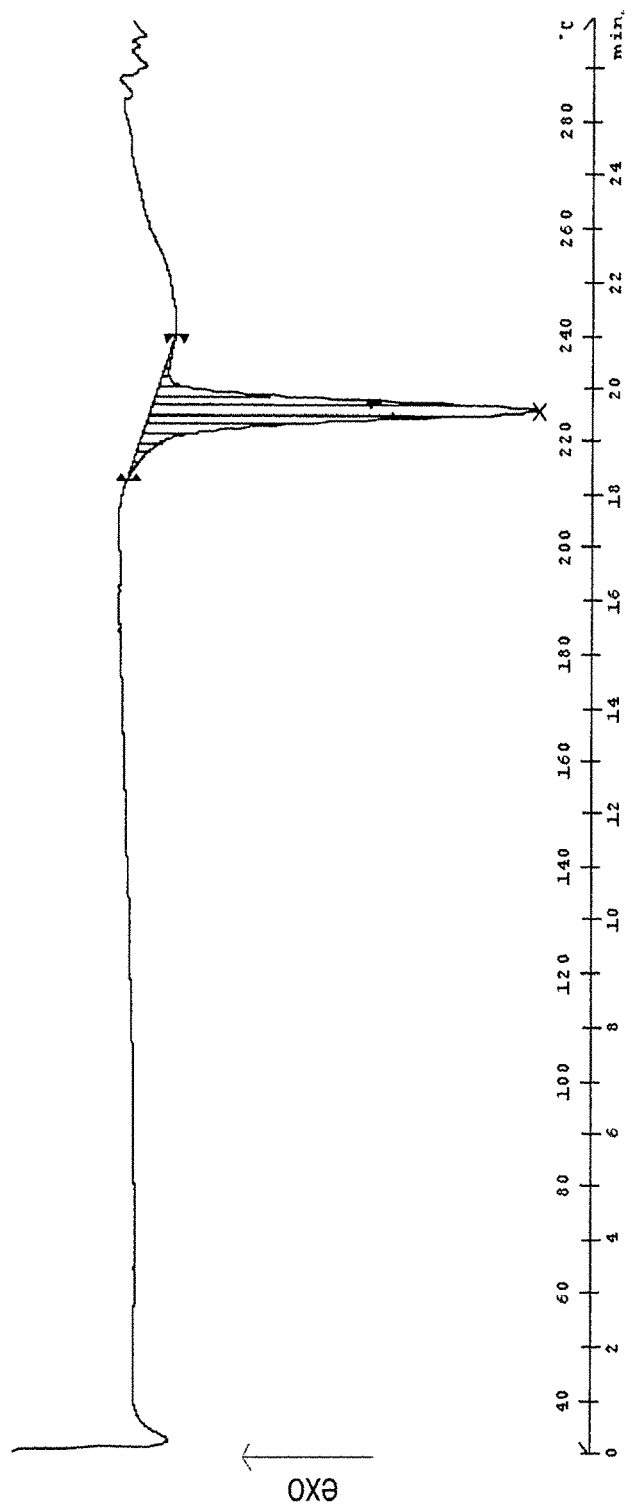
FIG. 28 Shows the differential scanning calorimetry analysis curve of the 2'-O-Fucosyllactose Polymorph C of Example 19

DSC=Initial flat profile, an indicator of the anhydrous state of the product, followed by an intense and narrow exothermic peak ($T_{onset}$=220.90° C.; $T_{peak}$=222.80° C.) attributable to its melting and an indicator of its high degree of crystallinity. See FIG. 28

Figure 29:
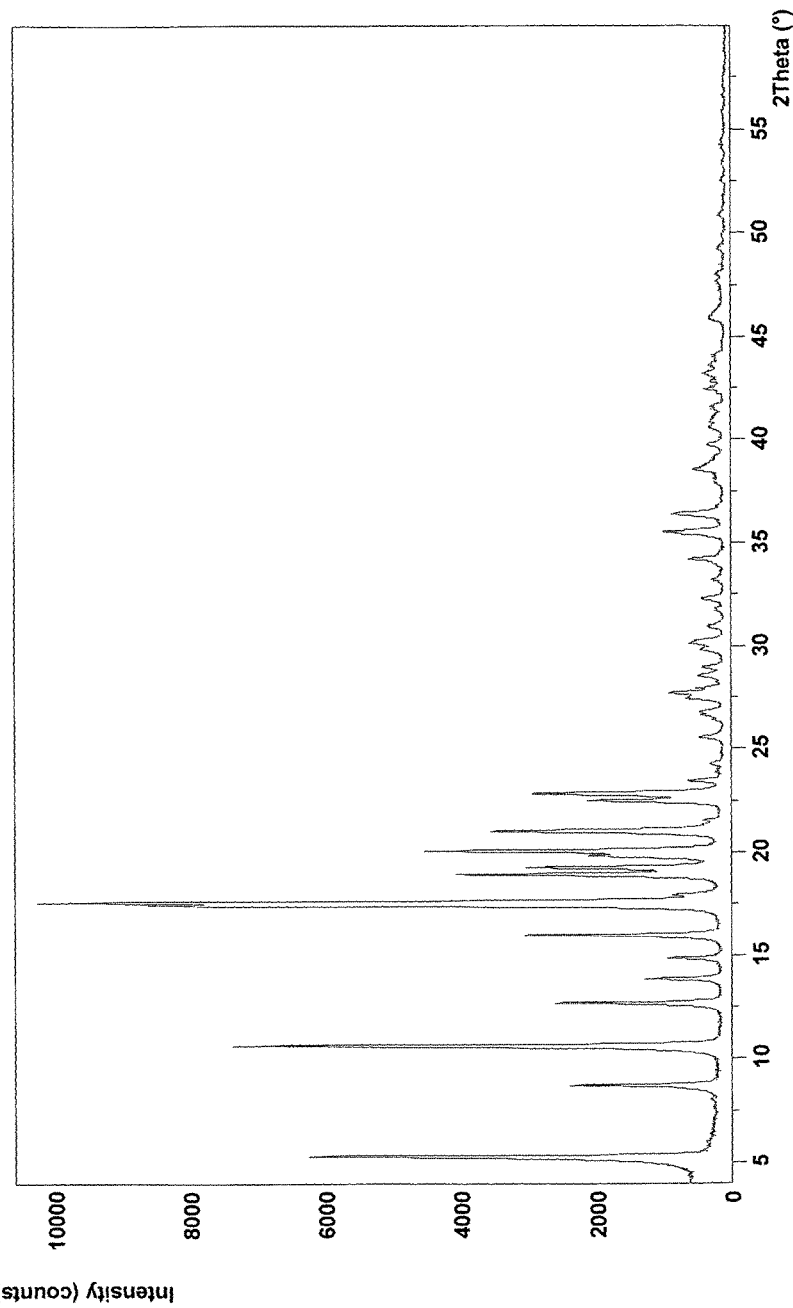
FIG. 29 Shows the X-ray powder diffraction spectrum of the 2'-O-Fucosyllactose Polymorph C of Example 19
Figure 30:
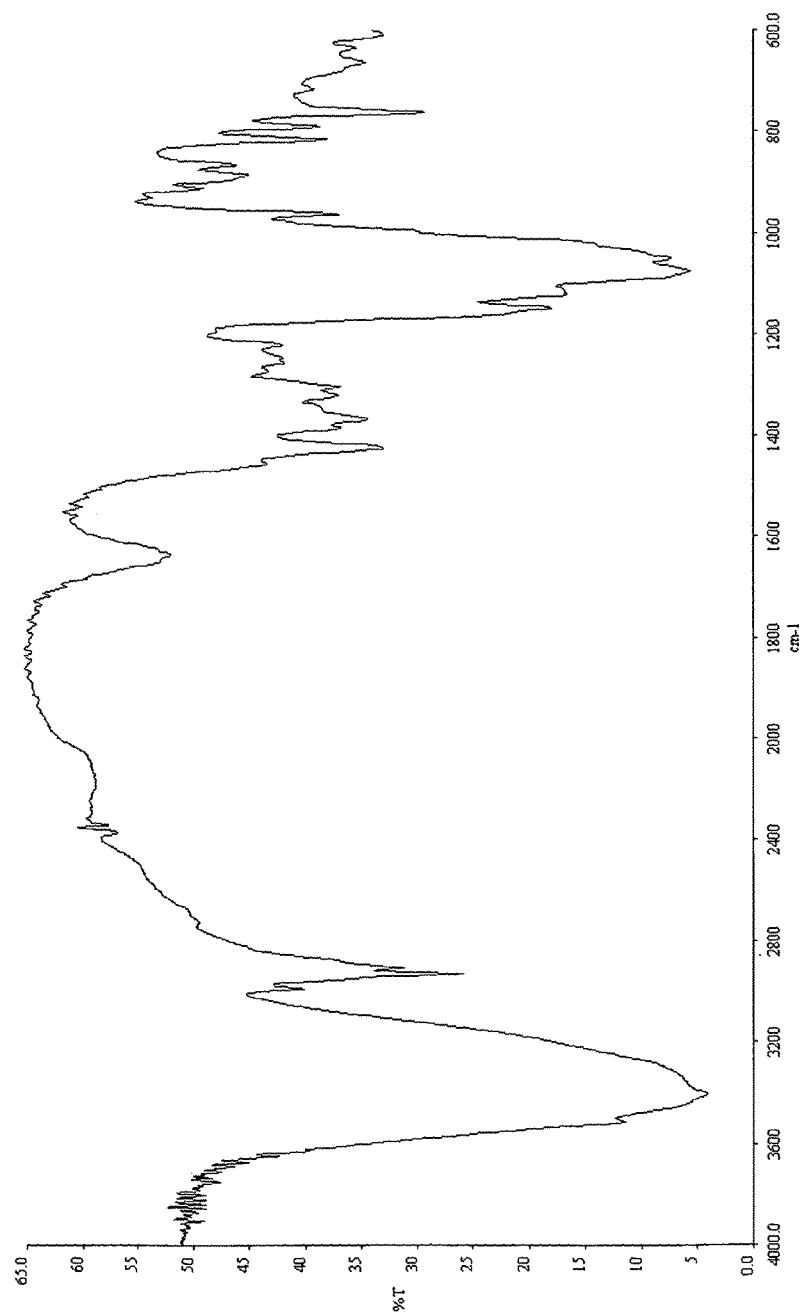
FIG. 30 Shows the IR spectrum of the 2'-O-Fucosyllactose Polymorph C of Example 20

Powder spectrum: Shows the phase of the anhydrous Polymorph C.

a (Å)=5.058(1)
b (Å)=12.773(3)
c (Å)=16.692(5)
α(°)=90
β(°)=94.743(8)
γ(°)=90
See FIG. 29

Example 20

Figure 31:
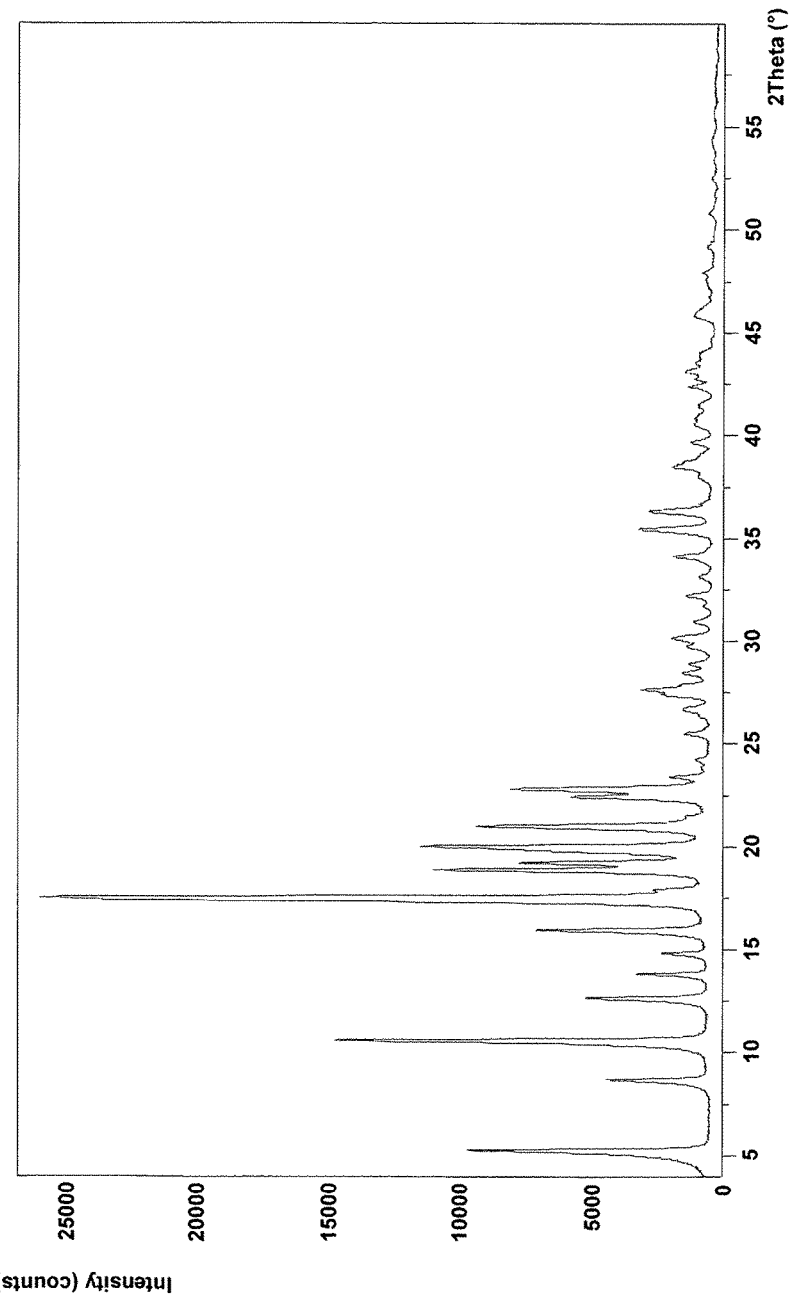
FIG. 31 Shows the X-ray powder diffraction spectrum of the 2'-O-Fucosyllactose Polymorph C of Example 20

5 grams of 2'-O-Fucosyllactose dried from syrup were dissolved with 10 volumes of methanol. The solution was brought to 40° C. and after 3-4 hours gave abundant precipitate. The suspension was brought to r.t. in 4 hours and cooled to 10-15° C. to then be filtered and washed with methanol. The solid was dried in a vacuum (80 mbar) at 50° C. to give 3.77 g of dry product, stored for the first 24 hours in a desiccator KF=0.99%
LOD=1.31% (IPTG)
PF=214-215
$^1$HNMR (D$_2$O) at dissolution (300 MHz, nt=12): α anomer/β anomer=14/86;
$^1$HNMR (DMSO) at dissolution (200 MHz; nt=8): α anomer/β anomer=16/84
IR=3403, 4; 2931, 26; 1637, 52; 1426, 33; 1369, 34, 1306, 37; 1259, 42; 1149, 18; 1075, 6; 965, 37; 889, 45; 869, 46; 819, 38; 793, 39; 765, 29; 666, 35. See Figure Powder spectrum: shows the phase of the anhydrous Polymorph C. See FIG. 31

Polymorph I

Example 21

75 mL of glacial acetic acid heated to 60° C. were added in 15 mL portions to 7.5 g of 2'-fucosyllactose dried from syrup, over 30 minutes. The suspension was maintained at 60° C. for 1 hour and then the heating was turned off and it was slowly allowed to return to room temperature. After 10 hours under agitation at room temperature the mixture was filtered, and washed with 1 volume of glacial acetic acid.

The solid was dried at 60° C. under vacuum (80 mbar) for 3 hours and 24 hours at ambient temperature and pressure.

Figure 32:
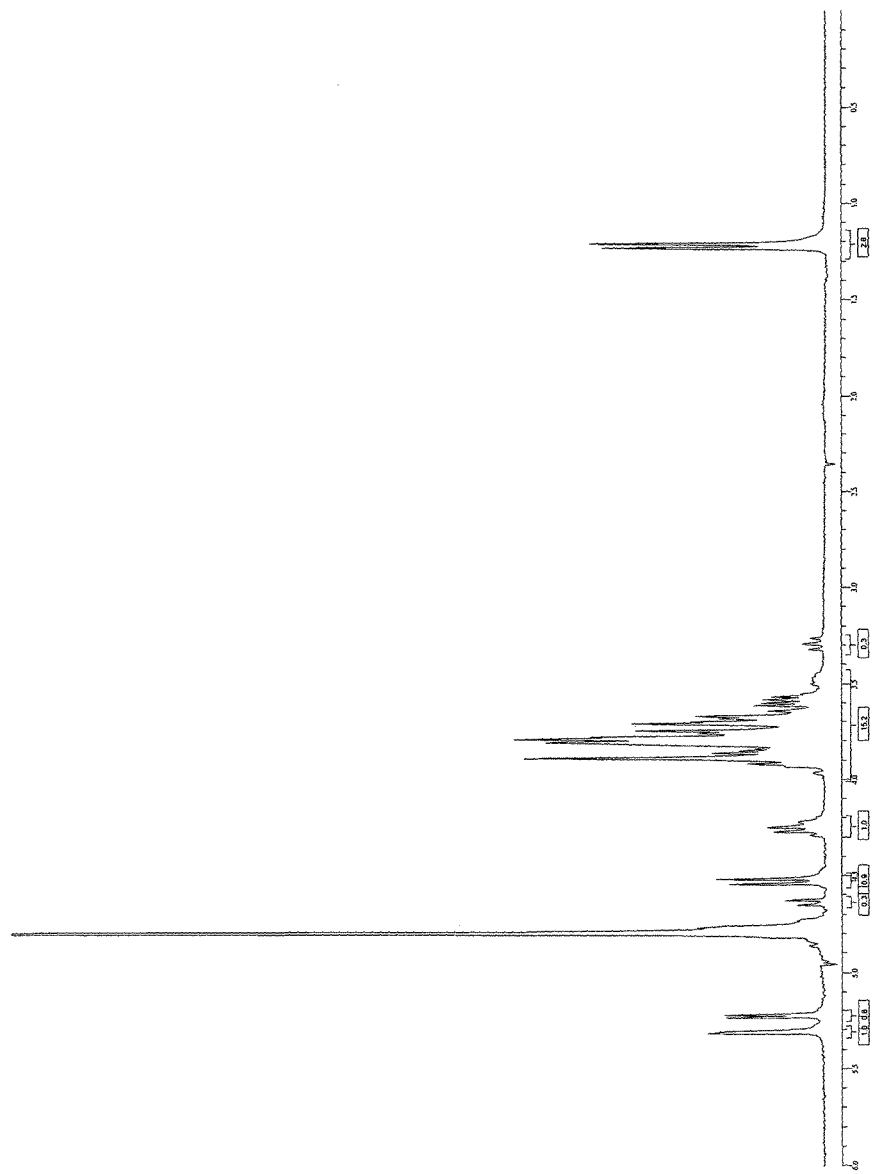
FIG. 32 Shows the $^1$HNMR spectrum of the 2'-O-Fucosyllactose Polymorph I of Example 21

6.7 g of solid were obtained.
KF=0.60%
KF after 10 days in a petri dish=0.67%
LOD=0.69% (Method 1)
LOD=0.47% (Method 2)
PF=218-226° C. decomposes
$^1$HNMR (D$_2$O) at dissolution (300 MHz; nt=16): α anomer/β anomer=75/25. See FIG. 32
$^1$HNMR (D$_2$O) at equilibrium after one night at room temperature (300 MHz, nt=16): α anomer/β anomer=46/54
$^1$HNMR (DMSO) at dissolution (300 MHz; nt=12): α anomer/β anomer=76/24
$^1$HNMR (DMSO) at equilibrium after one night at room temperature (200 MHz, nt=12): α anomer/β anomer=73/27

Figure 33:
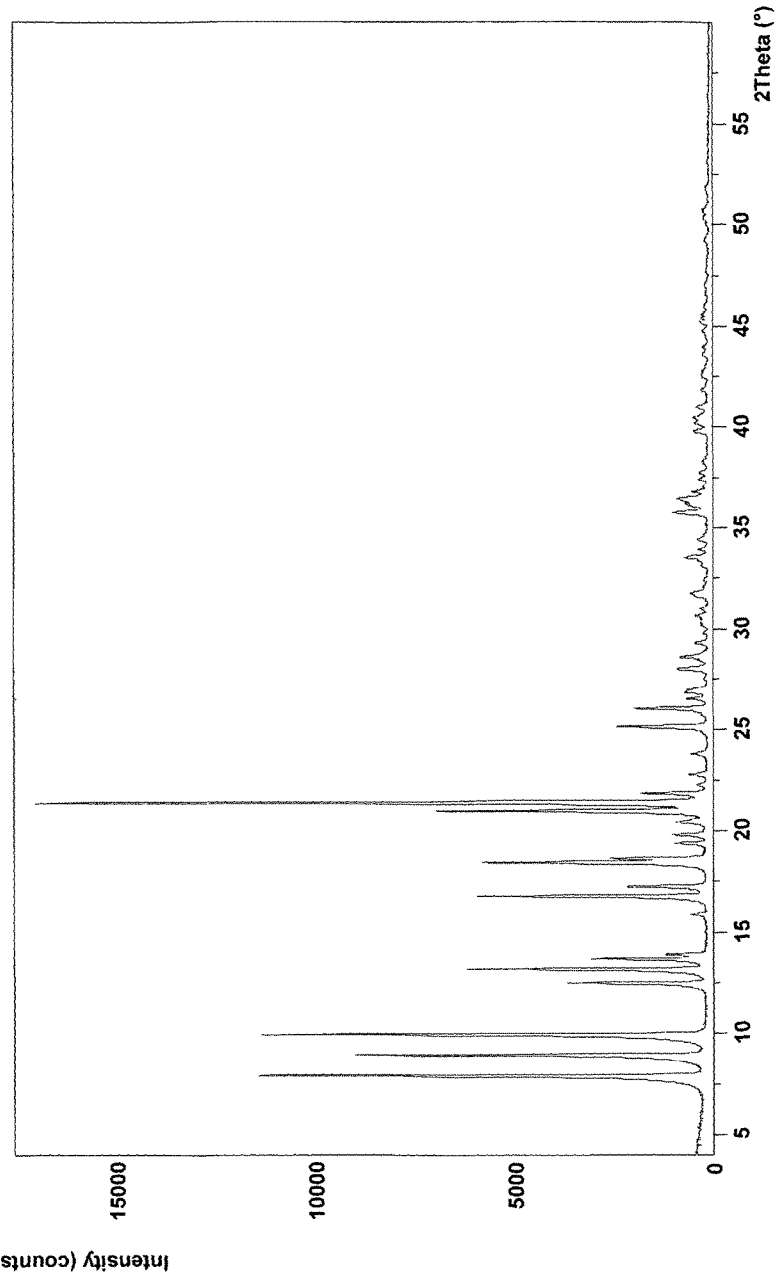
FIG. 33 Shows the X-ray powder diffraction spectrum of the 2'-O-Fucosyllactose Polymorph I of Example 21

Powder spectrum: Shows the phase of Polymorph I (See FIG. 33) which clearly implies that it corresponds to that reported in WO/2011 150939.

The invention claimed is:

1. A crystalline 2'-O-Fucosyllactose (2'FL)hydrate with molecular formula $C_{18}H_{32}O_{15} \cdot nH_2O$ wherein n is 3/2 in form of polymorph A, wherein said polymorph A is 2'FL·3/2H$_2$O, having characteristic XRPD peaks at 18.86±0.20, 9.89±0.20, 17.05±0.20 2θ.

2. The crystalline 2'FL according to claim 1, having further characteristic XRPD peaks at 21.65±0.2, and 14.20±0.20 2θ.

3. The crystalline 2'FL according to claim 1, wherein a single crystal of said crystalline 2'FL has a $P2_12_12_1$ spatial group which is arranged within an orthorhombic crystalline system and said crystal comprises elementary cells having the following parameters: a=12.4098(8) Å, b=12.737(2) Å, c=13.756(2) Å and a volume of 2212.5 Å$^3$.

4. The crystalline 2'FL according to claim 1, having β anomeric conformation.

5. A pharmaceutical or nutritional or cosmetic composition comprising 2'FL hydrate according to claim 1 and at least one other pharmaceutically, cosmetic or nutritionally acceptable ingredient.

6. A method for obtaining the 2'-O-Fucosyllactose (2'FL) hydrate of claim 1, comprising preparing an aqueous solution of 2'FL at a concentration by weight between 53% and 75%, and a temperature between 50° C. and 60° C.;
  adding at least one warm solvent or a solvent at boiling temperature to obtain a 2'FL crystallization mixture, wherein said warm solvent or said solvent at boiling temperature is selected from the group consisting of methanol, ethanol, propanol, acetone acetonitrile and acetic acid; further comprising keeping said 2'FL crystalline mixture and said solvent at a temperature between 50° C. and 60° C.;
  heating said 2'FL crystallization mixture to a temperature between 55° C. and 65° C. for 1-16 hours to obtain formation of crystallization nuclei and allowing the 2'FL crystallization mixture to cool at room temperature to obtain polymorph A via precipitation; and
  isolating precipitated polymorph A by filtration, washing and drying.

7. The method according to claim 6, wherein the warm solvent or solvent at boiling temperature is selected from the group consisting of methanol, ethanol, and propanol.

8. The method according to claim 6, wherein said warm solvent or solvent at boiling temperature added to said aqueous solution of 2'FL contains between 10 and 40% (v/v) of water.

9. A crystalline 2'-O-Fucosyllactose (2'FL) hydrate with molecular formula $C_{18}H_{32}O_{15} \cdot nH_2O$ wherein n is 5/2, in form of polymorph B, wherein said polymorph B is 2'FL.5/2 H$_2$O, having characteristic XRPD peaks at 9.96±0.20, 18.56±0.2, and 20.48+0.20 2θ.

10. The polymorph B according to claim 9, having further characteristic XRPD peaks at 14.21±0.20, and 11.90±0.20 2θ.

11. The polymorph B according to claim 9, wherein single crystal of said crystalline 2'FL has a $P2_12_12_1$ spatial group which is arranged within an orthorhombic crystalline system and said crystal comprises elementary cells having the following parameters: a=14.905(7) Å, b=12.663(6) Å, c=12.447(5) Å and a volume of 2349.4 Å$^3$.

12. The polymorph B according to claim 9, having β anomeric conformation.

13. A pharmaceutical or nutritional or cosmetic composition comprising 2'FL hydrate according to claim 9 and at least one other pharmaceutically, cosmetic or nutritionally acceptable ingredient.

14. A method for obtaining polymorph B according to claim 9, said method comprising
  (a) preparing a warm aqueous solution of 2'FL, said 2'FL present in said solution at a concentration of 50-80% by weight,
  (b) keeping the aqueous solution at 30-60° C. for 1-12 hours,
  (c) cooling the solution to a temperature between 20 and 30° C. for a period of time from 1 hours to 10 days to obtain polymorph B via precipitation, followed by;
  (d) cooling the mixture to a temperature between 2 and 18° C. and;
  (e) collecting precipitated polymorph B by filtration, washing and drying; said washing being carried out using water at 4-15° C.

15. The method of claim 14, further comprising seeding the aqueous solution of (b) with 2'FL polymorph B to facilitate formation of polymorph B crystals.

* * * * *